[12] United States Patent
Furusako et al.

(10) Patent No.: US 6,916,628 B1
(45) Date of Patent: Jul. 12, 2005

(54) METHOD FOR THE MEASUREMENT OF SOLUBLE CD14 PROTEINS SEPARATELY

(75) Inventors: Shouji Furusako, Tokyo (JP); Kamon Shirakawa, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 314 days.

(21) Appl. No.: 09/806,158

(22) PCT Filed: Sep. 18, 2000

(86) PCT No.: PCT/JP00/06359

§ 371 (c)(1),
(2), (4) Date: Mar. 28, 2001

(87) PCT Pub. No.: WO01/22085

PCT Pub. Date: Mar. 29, 2001

(30) Foreign Application Priority Data

Sep. 17, 1999  (JP) ........................................... 11/264474

(51) Int. Cl.[7] .......................... C07K 16/28; C12P 21/08; G01N 33/50; G01N 33/543; G01N 33/577

(52) U.S. Cl. ........................ 435/7.94; 435/7.1; 435/7.8; 435/70.21; 435/452; 435/334; 435/335; 435/343; 436/518; 436/528; 436/547; 436/548; 436/86; 530/388.22; 530/388.23; 530/388.7; 530/389.2

(58) Field of Search ............................... 435/7.1, 7.24, 435/7.8, 7.94, 70.21, 452, 331, 334, 335, 343; 436/518, 528, 548, 547, 86; 530/388.22, 388.23, 388.7, 389.2

(56) References Cited

FOREIGN PATENT DOCUMENTS

| EP | 0 911 400 A1 | 4/1999 |
|---|---|---|
| JP | A5501399 | 3/1993 |
| JP | A8510909 | 11/1996 |
| JP | 8-510909 | 11/1996 |
| JP | A10505839 | 6/1998 |
| WO | WO94/28025 A1 | 12/1994 |
| WO | WO 96/32418 A | 10/1996 |
| WO | WO98/39438 | 9/1998 |
| WO | WO01/72993 A1 | 10/2001 |

OTHER PUBLICATIONS

Regine Landmann et al., The Journal of Infectious Diseases; vol. 171, (1995), pp. 639–644.
Felix Stelter et al., Eur. J. Biochem., vol. 236, (1996), pp. 457–464.
Christine Schutt, Allerg. Immunol., vol. 34, (1988), pp. 17–26, abstract only.
Wesley C. Van Voorhis et al., J. Exp. Med., vol. 158, (Jul. 1983), pp. 126–145.
Todd S.C. Juan et al., The Journal of Biological Chemistry, vol. 270, No. 29, (Jul. 21, 1995), pp. 17237–17242.
Todd S.C. Juan et al., The Journal of Biological Chemistry, vol. 270, No. 10, (Mar. 10, 1995), pp. 5219–5224.
U. Grunwald et al., Journal of Immunological Methods, vol. 155, (1992), pp. 225–232.
Landmann R et al: Infection and Immunity, American Society for Microbiology, Washington, US, vol. 66, No. 5, May 1998, pp. 2264–2271, XP000882503.
Ferrero E et al: Nucleic Acids Research, Oxford University Press, Surrey, GB, vol. 16, No. 9, 1988, p. 4173, XP002916988.

*Primary Examiner*—Christopher L. Chin
*Assistant Examiner*—James L. Grun
(74) *Attorney, Agent, or Firm*—Birch, Stewart, Kolasch & Birch, LLP

(57) ABSTRACT

The present invention provides a method for qualitative determination of low molecular weight soluble CD14 proteins separately. The present invention also provides antibodies specific to high molecular weight soluble CD14 proteins. Further, the present invention provides a measurement method for specifically determining the quality or quantity of high molecular weight soluble CD14 proteins using the antibodies with high sensitivity, simplicity and specificity.

15 Claims, 4 Drawing Sheets

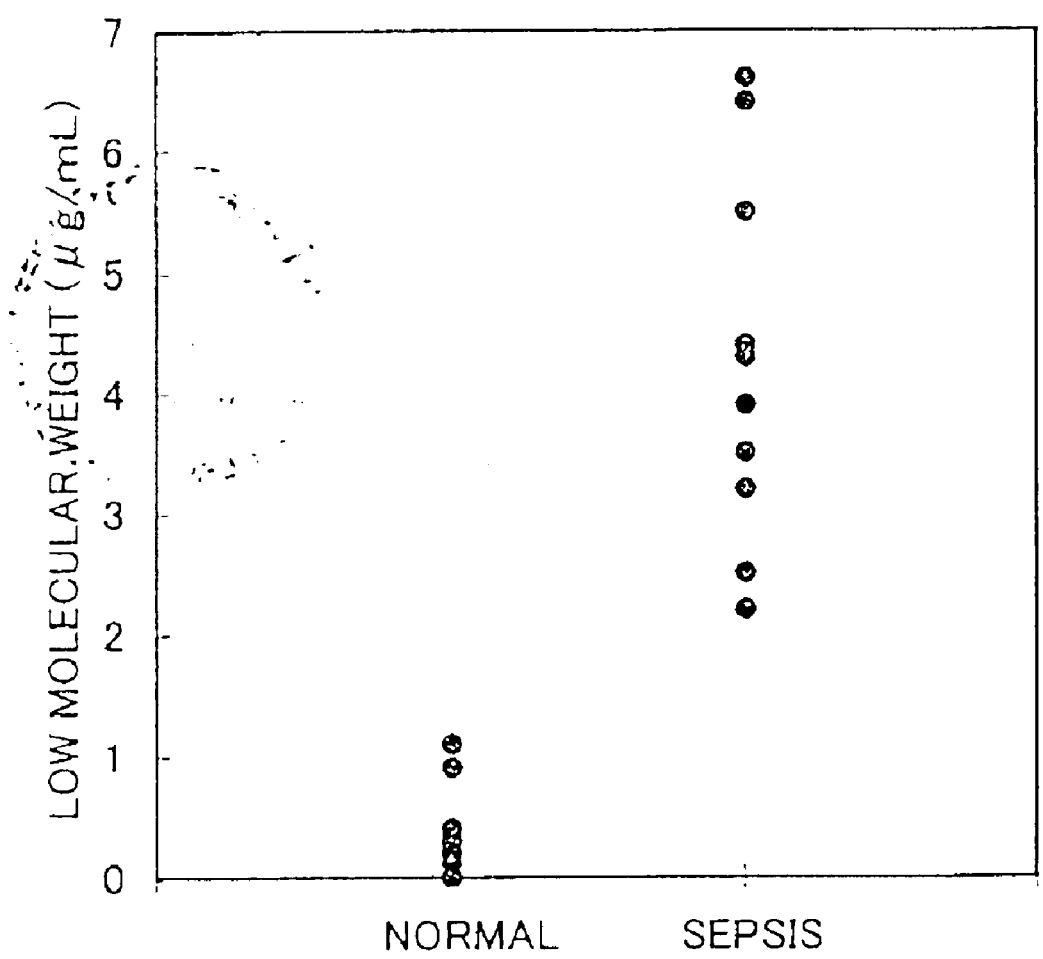

SEQUENCE LISTING

<160> NUMBER OF SEQ ID NOS: 13

<210> SEQ ID NO 1
<211> LENGTH: 356
<212> TYPE: PRT
<213> ORGANISM: Homo sapiens

```
<400> SEQUENCE: 1

Thr Thr Pro Glu Pro Cys Glu Leu Asp Asp Glu Asp Phe Arg Cys Val
1               5                   10                  15

Cys Asn Phe Ser Glu Pro Gln Pro Asp Trp Ser Glu Ala Phe Gln Cys
            20                  25                  30

Val Ser Ala Val Glu Val Glu Ile His Ala Gly Gly Leu Asn Leu Glu
        35                  40                  45

Pro Phe Leu Lys Arg Val Asp Ala Asp Ala Asp Pro Arg Gln Tyr Ala
    50                  55                  60

Asp Thr Val Lys Ala Leu Arg Val Arg Arg Leu Thr Val Gly Ala Ala
65                  70                  75                  80

Gln Val Pro Ala Gln Leu Leu Val Gly Ala Leu Arg Val Leu Ala Tyr
                85                  90                  95

Ser Arg Leu Lys Glu Leu Thr Leu Glu Asp Leu Lys Ile Thr Gly Thr
            100                 105                 110

Met Pro Pro Leu Pro Leu Glu Ala Thr Gly Leu Ala Leu Ser Ser Leu
            115                 120                 125

Arg Leu Arg Asn Val Ser Trp Ala Thr Gly Arg Ser Trp Leu Ala Glu
            130                 135                 140

Leu Gln Gln Trp Leu Lys Pro Gly Leu Lys Val Leu Ser Ile Ala Gln
145                 150                 155                 160

Ala His Ser Pro Ala Phe Ser Cys Glu Gln Val Arg Ala Phe Pro Ala
                165                 170                 175

Leu Thr Ser Leu Asp Leu Ser Asp Asn Pro Gly Leu Gly Glu Arg Gly
            180                 185                 190

Leu Met Ala Ala Leu Cys Pro His Lys Phe Pro Ala Ile Gln Asn Leu
            195                 200                 205

Ala Leu Arg Asn Thr Gly Met Glu Thr Pro Thr Gly Val Cys Ala Ala
            210                 215                 220

Leu Ala Ala Gly Val Gln Pro His Ser Leu Asp Leu Ser His Asn
225                 230                 235                 240

Ser Leu Arg Ala Thr Val Asn Pro Ser Ala Pro Arg Cys Met Trp Ser
                245                 250                 255

Ser Ala Leu Asn Ser Leu Asn Leu Ser Phe Ala Gly Leu Glu Gln Val
            260                 265                 270

Pro Lys Gly Leu Pro Ala Lys Leu Arg Val Leu Asp Leu Ser Cys Asn
            275                 280                 285

Arg Leu Asn Arg Ala Pro Gln Pro Asp Glu Leu Pro Glu Val Asp Asn
            290                 295                 300

Leu Thr Leu Asp Gly Asn Pro Phe Leu Val Pro Gly Thr Ala Leu Pro
305                 310                 315                 320

His Glu Gly Ser Met Asn Ser Gly Val Val Pro Ala Cys Ala Arg Ser
                325                 330                 335

Thr Leu Ser Val Gly Val Ser Gly Thr Leu Val Leu Leu Gln Gly Ala
            340                 345                 350

Arg Gly Phe Ala
        355

<210> SEQ ID NO 2
<211> LENGTH: 20
<212> TYPE: DNA
<213> ORGANISM: Artificial Sequence
<220> FEATURE:
<223> OTHER INFORMATION: Primer sequence targeted to Homo sapiens
```

<400> SEQUENCE: 2
cacgccagaa ccttgtgagc                                            20

<210> SEQ ID NO 3
<211> LENGTH: 30
<212> TYPE: DNA
<213> ORGANISM: Artificial Sequence
<220> FEATURE:
<223> OTHER INFORMATION: Primer sequence targeted to Homo sapiens

<400> SEQUENCE: 3
gtcagtgcac aggctggcta ttagccggag                                 30

<210> SEQ ID NO 4
<211> LENGTH: 38
<212> TYPE: DNA
<213> ORGANISM: Artificial Sequence
<220> FEATURE:
<223> OTHER INFORMATION: Primer sequence targeted to Homo sapiens

<400> SEQUENCE: 4
gtcagtgcac aggctgggac cacaacggat tgcattga                        38

<210> SEQ ID NO 5
<211> LENGTH: 30
<212> TYPE: DNA
<213> ORGANISM: Artificial Sequence
<220> FEATURE:
<223> OTHER INFORMATION: Primer sequence targeted to Homo sapiens

<400> SEQUENCE: 5
cccaagcttc tattagagat cgagcactct                                 30

<210> SEQ ID NO 6
<211> LENGTH: 8
<212> TYPE: PRT
<213> ORGANISM: Homo sapiens

<400> SEQUENCE: 6

Ser Thr Leu Ser Val Gly Val Ser
1               5

<210> SEQ ID NO 7
<211> LENGTH: 6
<212> TYPE: PRT
<213> ORGANISM: Homo sapiens

<400> SEQUENCE: 7

Ala Leu Pro His Glu Gly
1               5

<210> SEQ ID NO 8
<211> LENGTH: 10
<212> TYPE: PRT
<213> ORGANISM: Artificial Sequence
<220> FEATURE:
<223> OTHER INFORMATION: sequence derived from Homo sapiens

<400> SEQUENCE: 8

Ala Cys Ala Arg Ser Thr Leu Ser Val Gly
1               5                   10

<210> SEQ ID NO 9
<211> LENGTH: 10

```
-continued

<212> TYPE: PRT
<213> ORGANISM: Artificial Sequence
<220> FEATURE:
<223> OTHER INFORMATION: sequence derived from Homo sapiens

<400> SEQUENCE: 9

Ala Arg Ser Thr Leu Ser Val Gly Val Ser
1               5                   10

<210> SEQ ID NO 10
<211> LENGTH: 10
<212> TYPE: PRT
<213> ORGANISM: Artificial Sequence
<220> FEATURE:
<223> OTHER INFORMATION: sequence derived from Homo sapiens

<400> SEQUENCE: 10

Ser Thr Leu Ser Val Gly Val Ser Gly Thr
1               5                   10

<210> SEQ ID NO 11
<211> LENGTH: 10
<212> TYPE: PRT
<213> ORGANISM: Artificial Sequence
<220> FEATURE:
<223> OTHER INFORMATION: sequence derived from Homo sapiens

<400> SEQUENCE: 11

Val Pro Gly Thr Ala Leu Pro His Glu Gly
1               5                   10

<210> SEQ ID NO 12
<211> LENGTH: 10
<212> TYPE: PRT
<213> ORGANISM: Artificial Sequence
<220> FEATURE:
<223> OTHER INFORMATION: sequence derived from Homo sapiens

<400> SEQUENCE: 12

Gly Thr Ala Leu Pro His Glu Gly Ser Met
1               5                   10

<210> SEQ ID NO 13
<211> LENGTH: 10
<212> TYPE: PRT
<213> ORGANISM: Artificial Sequence
<220> FEATURE:
<223> OTHER INFORMATION: sequence derived from Homo sapiens

<400> SEQUENCE: 13

Ala Leu Pro His Glu Gly Ser Met Asn Ser
1               5                   10
```

US 6,916,628 B1

METHOD FOR THE MEASUREMENT OF SOLUBLE CD14 PROTEINS SEPARATELY

This application is the national phase under 35 U.S.C. §371 of PCT International Application No. PCT/JP00/06359 which has an International filing date of Sep. 18, 2000, which designated the United States of America.

TECHNICAL FIELD

The present invention relates to a method for the fractional assay of a low molecular weight soluble CD14 protein. More particularly, the present invention relates to a method for the assay of low molecular weight soluble CD14 proteins separately by measuring the total amount of soluble CD14 proteins in the body fluid and subtracting therefrom the amount of a high molecular weight soluble CD14 protein measured by a measuring system specific to the high molecular weight soluble CD14 protein. The present invention also relates to a method for diagnose the sepsis using the above-described measuring method. Also, the present invention relates to an antibody that has a specific bindability to the C-terminus of a high molecular weight soluble CD14 protein, to a cell producing the same and to use of the antibody. More specifically, the present invention relates to a hybridoma that produces a monoclonal antibody to the region of from glycine at the 316th position to alanine at the 356th position in the sequence of a high molecular weight soluble CD14 protein. Further, the present invention relates to a polypeptide consisting of any consecutive 6 to 41 amino acids from among 41 amino acids sequence from glycine at the 316th position to alanine at the 356th position in the sequence of a high molecular weight soluble CD14 protein. Furthermore, the present invention relates to use of the monoclonal antibody in the step of measuring the amount of a high molecular weight soluble CD14 protein in the method for the measurement of a low molecular weight soluble CD14 protein. Moreover, the present invention relates to a measurement method that specifically determines the quality or quantity of a high molecular weight soluble CD14 protein using the monoclonal antibody.

BACKGROUND ART

In 1990, Wright et al. elucidated that a 53 kDa glycoprotein named CD14 expressed on the membrane of a monocyte is a receptor for LPS, which is an endotoxin (Science 249: p.1431, 1990). The CD14 protein includes a soluble CD14 protein (hereinafter, also referred to as sCD14 protein or soluble CD14 protein) in addition to a membrane bound type CD14 protein (hereinafter, also referred to as mCD14 protein). It has been reported that in blood there are a plurality of soluble CD14 proteins differing in molecular weight (Labeta MO, Eur. J. Immunol., 23, 2144, 1993). The soluble CD14 proteins were considered to be CD14 proteins on the membrane that were released due to the activation of the cell. On the contrary, it has recently been reported that mCD14 protein is expressed on primary human liver cells and liver cell lines (Su GL, J. Hematology, 31, 435, 1999). In a transgenic mouse in which an 80 kb genomic human CD14 protein containing the 5' and 3' flanking regions of the gene of CD14 protein were introduced, mCD14 proteins were expressed not only in monocytes/macrophages but also in liver cells (Hetherlington C, et al., J. Immunol., 162, 503, 1999). Also, it has hitherto been considered that sCD14 proteins trap LPS in the blood and transport it to HDL so that clearance of LPS is made in the liver (J. Exp. Med., 181, 1743, 1995).

Thus, as its physiological function, while the soluble CD14 protein directly or indirectly clears LPS, a complex of LPS and sCD14 protein bound thereto (sCD14 protein/LPS) considerably activates macrophages through mCD14 proteins on the macrophages to induce inflammatory cytokines (Hailmann, E. et al., J. Immunol., 156, 4384, 1996). Further, the sCD14 protein/LPS induces cellular death of vascular endothelial cells or vascular smooth muscle cells and production of inflammatory cytokines (Loppnow, H. et al., Infection & Immunity, 63, 1020, 1995). The vascular endothelial cells and vascular smooth muscle cells were confirmed to have no mCD14 protein, so that existence of a receptor that recognizes sCD14 protein/LPS was suggested (Tobias et al., J. Exp. Med., 178, 2193, 1993). Also, there is a report that the endothelial cells of a patient with hemoglobin nocturnal enuresis (PNH) who is suffering from GPI biosynthesis failure has an LPS response with a sCD14 protein (J. Lab. Clin. Med., 125, 662, 1995).

Recently, it has been found that CD14 proteins recognize phosphatidylserine and contributes to the removal of cells that caused apoptosis. Thus a function of CD14 protein other than that as LPS receptor has been elucidated (Devitt A, Nature, 392, 505, 1998). Moreover M. Labeta et al. reported that sCD14 proteins have an activity of suppressing T cell activator (M. Labeta, et al., Eur. J. Immunol. 29, 265, 1999).

Reportedly, soluble CD14 proteins increase in sera or urines of patients with sepsis, external injuries, burn injuries, or rheumatism and are considered to participate in the exclusion of LPS or in LPS signal transfer. Landmann et al. conducted Western analysis of soluble CD14 proteins of the serum from a patient with sepsis and reported that a high molecular weight soluble CD14 protein is at high levels in death cases from sepsis or patients with paroxysmal nocturnal hemoglobinuria (PNH) and that in normal sera, there was detected no high molecular weight soluble CD14 protein that was detected in death cases from sepsis (The Journal of Infectious Disease, Vol. 171, p. 639, 1995). Existence of the subtypes differing in molecular weight is attributable to a difference in glyco chain and after the removal of N and 0 bound type glyco chain, there are still two kinds of soluble CD14 proteins differing in molecular weight as reported by Stelter et al. (Eur. J. Biochem., Vol. 236, p.457, 1996). Buffler et al. performed C-terminus analysis of a soluble CD14 protein and reported that a GPI group binds to the serine residue at the 327th position of the soluble CD14 protein and that a soluble CD14 protein having a molecular weight of about 56 kDa is a molecule species that is not GPI anchored (Eur. J. Immunol., Vol. 25, p.604, 1995).

As described above, given that there is such a report that a subtype of a high molecular weight soluble CD14 protein in blood is at high levels in sera of patients suffering from sepsis in severe cases, it is suggested that measurement of soluble CD14 proteins will be clinically important. However, these analyses have the problem that they are by a Western method, which requires complicated operational process and is low in sensitivity, thus they are impractical. That is, since there has been no specific measurement method that is highly sensitive but simple and easy, clinical usefulness of measurement of soluble CD14 proteins could not be proved. Therefore, to prove the clinical usefulness of high molecular weight soluble CD14 proteins, development of a method for measuring them with high sensitivity, simply and easily, and specifically has been required.

As antibodies to soluble CD14 proteins, there have been prepared many anti-CD14 protein antibodies in addition to MEM-18 prepared by Bazil et al. (Eur. J. Imunol., Vol. 16, p.1583, 1986), RoMo-1 prepared by Shutt et al. (Allerg.

Immunol. (Leipz), Vol. 34, No. 1, p.17, 1988), 3C10 prepared by Steinman et al. (J. Exp. Med., Vol. 158, No. 1, p.126, 1983). Published Translation of Japanese Patent Application No. Hei 8-510909 discloses 28C5, 23G4 and the like.

It has been elucidated that 3C10, MEM-18, 28C5 or 23G4 has an activity of inhibiting the binding of LPS to a CD14 protein. Particularly, 3C10 and MEM-18 have their respective binding regions on the side of amino termini, that is, in the amino acids 7–14, (J. Biol. Chem., Vol. 270, No. 29, p. 17237, 1995) and amino acids 57–64 (J. Biol. Chem., Vol. 270, No. 10, p. 5219, 1995) described in SEQ ID No. 1, which is the binding region for LPS. Also, a system for measuring soluble CD14 proteins using the antibodies (J. Immunol. Methods, Vol. 155, p. 225, 1992) has been prepared. Since the measurement systems using the antibodies use antibodies that recognize amino termini, the soluble CD14 proteins in the blood to be measured are all the soluble CD14 proteins that exist in blood (hereinafter, the soluble CD14 proteins measured with an antibody having specificity to the N-terminus are described as total amount). In other words, the antibodies to soluble CD14 proteins thus far reported recognize all the soluble CD14 proteins that are present in blood but do not specifically recognize high molecular weight soluble CD14 proteins, so that it is impossible to perform specific measurement of the high molecular weight soluble CD14 proteins using the antibodies.

Further, the present inventors have reported in Japanese Patent Application No. 2000-099617 that soluble CD14 protein (1–285) and low molecular weight soluble CD14 36 kDa protein have an activity of inhibiting the induction of inflammatory cytokines. It is considered that while the low molecular weight soluble CD14 36 kDa protein in blood directly or indirectly clears LPS as its physiological function, it also inhibits a complex of LPS and sCD14 protein bound thereto (sCD14 protein/LPS) from considerably activating macrophages through mCD14 proteins on the macrophages and inducing inflammatory cytokines. Further, since the sCD14 protein/LPS induces cellular death of vascular endothelial cells or vascular smooth muscle cells and production of inflammatory cytokines, the low molecular weight soluble CD14 36 kDa protein is considered to similarly inhibit the injuries of vascular endothelial cells and vascular smooth muscle cells. From the above, it is presumed that in patients suffering from sepsis, a mechanism exists, in which LPS stimulation enhances production of mCD14 protein on macrophages and thereafter the mCD14 protein is severed with protease to produce a low molecular weight soluble CD14 protein and the low molecular weight soluble CD14 protein is expected to work as a defense factor of an organism for inhibiting injuries of cells. Therefore, it is considered that an increase in the low molecular weight soluble CD14 protein (36 kDa) in patients suffering sepsis is a defense mechanism in an organism that is initiated by LPS stimulation, collapse of which mechanism aggravates the state of patients suffering from sepsis.

In other words, it is suggested that, like the measurement of the high molecular weight soluble CD14 proteins, measurement of the low molecular weight soluble CD14 proteins is also clinically important. However, the antibodies to soluble CD14 proteins thus far reported fail to specifically recognize the low molecular weight soluble CD14 proteins either. Moreover, although details will be described in DISCLOSURE OF THE INVENTION below, it is even more difficult to prepare antibodies that specifically recognize the low molecular weight soluble CD14 proteins than antibodies that specifically recognize the high molecular weight soluble CD14 proteins. For this reason, development of a method for measuring a low molecular weight soluble CD14 protein with high sensitivity, simply and easily and specifically has been demanded.

DISCLOSURE OF THE INVENTION

From the above, an object of the present invention is to provide a specific antibody to a high molecular weight soluble CD14 protein. Also, an object of the present invention is to provide a measurement method that determines the quality or quantity of a high molecular weight soluble CD14 protein with high sensitivity, simply and easily, and specifically using such an antibody. In addition, an object of the present invention is to provide a measurement method that determines the quality or quantity of a low molecular weight soluble CD14 protein.

As a result of intensive research, the present inventors have been successful in preparing an antibody that specifically recognizes a high molecular weight soluble CD14 protein and specifically measuring a high molecular weight soluble CD14 protein. Analysis of soluble CD14 proteins in blood using the antibody of the invention and the developed measuring system indicated that contrary to the report by Landmann et al., major molecule species of soluble CD14 proteins in the blood of normal person are high molecular weight soluble CD14 49 kDa protein and CD14 55 kDa protein. Also, it proved that in blood there exists a small amount of a low molecular weight soluble CD14 36 kDa protein, which occurs in a lesser amount in normal persons and in an increased amount in patients suffering from sepsis.

The low molecular weight soluble CD14 proteins are proteins derived from high molecular weight soluble CD14 proteins by cutting off the C-termini thereof and their amino acid sequences are those sequences preserved in the high molecular weight soluble CD14 proteins. That is, the low molecular weight soluble CD14 proteins have totally the same amino acid sequences as portions of the high molecular weight soluble CD14 proteins. Accordingly, the antibody of the present invention and antibodies thus far known are either those antibodies that recognize only high molecular weight soluble CD14 proteins or the ones that simultaneously recognize both high molecular weight soluble CD14 proteins and low molecular weight soluble CD14 proteins but no antibody has been known that recognizes only a low molecular weight soluble CD14 protein.

As described above, no antibody that specifically recognizes only a low molecular weight soluble CD14 protein has been known yet and at present it is difficult to prepare such an antibody by the analysis of its primary sequence. The soluble CD14 36 kDa protein, which is a major protein of the low molecular weight soluble CD14 proteins, has been discovered by the present inventors and there has been no available knowledge on the uniqueness of its structure, thus it is quite unclear as to whether or not antibodies that specifically recognize only low molecular weight soluble CD14 proteins can be prepared in future.

Therefore, the present inventors invented a method for determining low molecular weight soluble CD14 proteins by subtracting the amount of high molecular weight soluble CD14 proteins measured by a specific measurement system for high molecular weight soluble CD14 proteins using an antibody prepared by the present inventors that specifically recognizes only high molecular weight soluble CD14 proteins, from the total amount of soluble CD14 proteins measured by a conventional antibody, that is, soluble CD14 proteins, thus completing the present invention.

Hereinafter, the present invention will be described more specifically.

As described above, there are in human blood roughly 3 kinds of soluble CD14 proteins having molecular weights of 55 kDa, 49 kDa and 36 kDa, respectively. The present inventors analyzed soluble CD14 proteins in blood and elucidated that a major portion of it is occupied by high molecular weight soluble CD14 49 kDa protein and CD14 55 kDa protein and that only a small amount of a low molecular weight soluble CD14 36 kDa protein is contained therein.

As a result of intensive research, the present inventors have developed an antibody that specifically recognizes the high molecular weight soluble CD14 protein described in SEQ ID No. 1, a polypeptide that can be an epitope of the antibody, a hybridoma that produces the antibody, a measurement method for determining the quality or quantity of high molecular weight soluble CD14 proteins with high sensitivity, simply and easily, and specifically using the antibody, and a method for diagnosing diseases in which low molecular weight soluble CD14 proteins participate using the measurement method, thus completing the present invention.

That is, the present invention comprises the following measurement method, diagnostic method, polypeptide, antibody and hybridoma.

(1) A method for measurement of low molecular weight soluble CD14 proteins in a body fluid.
(2) The method for measurement as in (1) above, comprising steps of (A) to (C):
 (A) measuring the total amount of soluble CD14 proteins,
 (B) measuring the amount of high molecular weight soluble CD14 proteins by a system for specifically measuring high molecular weight soluble CD14 proteins, and
 (C) subtracting the amount of high molecular weight soluble CD14 proteins from the total amount of soluble CD14 proteins.
(3) The method for measurement as in (1) or (2) above, wherein the low molecular weight soluble CD14 protein is a soluble CD14 36 kDa protein.
(4) A method for diagnosing the sepsis, comprising measuring a low molecular weight soluble CD14 protein in a body fluid.
(5) An antibody that binds to a high molecular weight soluble CD14 protein but does not bind to low molecular weight soluble CD14 protein.
(6) The antibody as in (4) above, wherein the antibody binds to any one of C-terminal 41 amino acids portion in a full length soluble CD14 protein consisting of the amino acid sequence described in SEQ ID No. 1.
(7) The antibody as in (5) above, wherein any of the C-terminal 41 amino acids portion is an amino acid sequence of from the 316th to the 328th positions or an amino acid sequence of from the 331st to the 345th positions.
(8) The antibody as in any one of (5) to (7), wherein the antibody binds to a high molecular weight soluble CD14 protein but does not bind to a portion from the 1st to 315th positions of the amino acid sequence described in SEQ ID No. 1.
(9) The antibody as in (5) above, wherein the high molecular weight soluble CD14 protein is a soluble CD14 49 kDa protein and/or a soluble CD14 55 kDa protein, and wherein the low molecular weight soluble CD14 protein is a soluble CD14 36 kDa protein.
(10) A polypeptide comprising consecutive 6 to 41 amino acids from 41 amino acids sequence of from the 316th to the 356th in the amino acid sequence described in SEQ ID No. 1.

(11) A hybridoma that produces the antibody as in any one of (5) to (9) above.
(12) A method for specifically determining the quality or quantity of a high molecular weight soluble CD14 protein, characterized in comprising using the antibody as in any one of (5) to (9) above.
(13) The method for measurement as in (2) above, wherein the step (B) comprises a process of specifically determining the quantity of the high molecular weight soluble CD14 protein as in (12) above.

BRIEF DESCRIPTION OF THE DRAWINGS

FIG. 7 is a diagram illustrating results of measurement of low molecular weight soluble CD14 proteins in normal persons and patients suffering from sepsis obtained by subtracting the amount of high molecular weight soluble CD14 proteins measured by a sandwich ELISA system using monoclonal antibody F1023-1-1 and F1025-3-1 antibody from the total amount of soluble CD14 proteins measured using the kit available from IBL Co.

DESCRIPTION OF THE MOST PREFERRED EMBODIMENT

Figure 1:
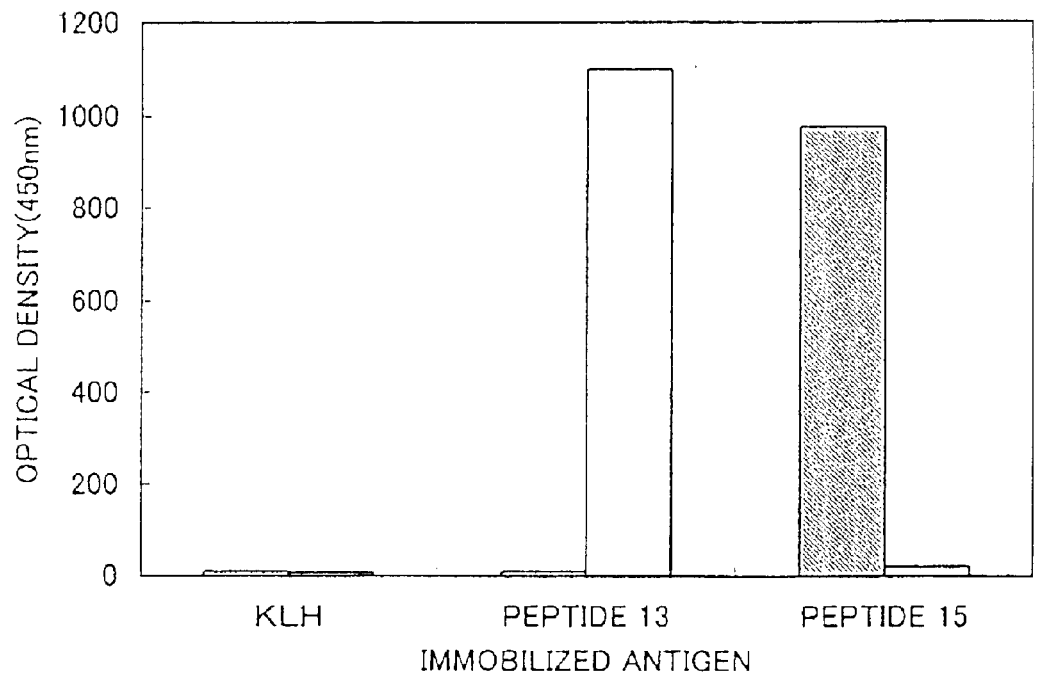
FIG. 1 is a diagram illustrating results of measurement of the specificity of monoclonal antibodies F1033-3-1 and F1025-3-1 by an ELISA method based on the reactivity with peptide carriers (KLH, peptide 13, and peptide 15) used as immunogens.

Hereinafter, the present invention will be described in more detail.

A first embodiment of the present invention relates to an antibody that binds to a high molecular weight soluble CD14 protein but does not bind to any low molecular weight soluble CD14 protein. The high molecular weight soluble CD14 protein means a soluble CD14 protein obtained as a result of processing of an N-terminal signal peptide of a human CD14 protein and of its extracellular secretion or expression. Human full length soluble CD14 protein consisting of 356 amino acid residues described in SEQ ID No. 1 and those proteins derived from this protein with the C-terminus having 41 amino acids or less being processed comprise the high molecular weight soluble CD14 protein. It is known that humans have a diversity of allele mutations and those proteins with one or more amino acids substituted, deleted or added are also included in the high molecular weight soluble CD14 protein. Major protein thereof includes a soluble CD14 55 kDa protein and a soluble CD14 49 kDa protein. However, it is not limited to these.

The low molecular weight soluble CD14 protein is a protein obtained by deleting 42 or more amino acids from the C-terminus of human full length soluble CD14 protein. In the same manner as above, those proteins with one or more amino acids substituted, deleted or added are also included in the low molecular weight soluble CD14 protein. Major protein thereof includes a 36 kDa protein in the analysis of human blood as shown in Example 11 and FIG. 6. However, as shown in Example 12, a plurality of bands were confirmed in addition to the main 36 kDa protein in the analysis of human urine, so that it is not particularly limited.

As a result of anticipation of secondary structure of a human CD14 protein using the GOR IV method by Garner et al. (Methods in Enzymology, Vol. 266, p. 540, 1996), it has been found that a β sheet is formed in the amino acid residues of the 312th to the 314th positions and of the 329th to 330th positions. Further, as a result of CLUSTALW's multiple alignment of 5 types of amino acid sequences, i.e., human, bovine, rabbit, mouse and rat CD14 proteins, it has been found that the amino acids 315 to 329 were deleted. The fact that the sequence is not preserved among species and the above anticipation of structure collectively suggest the possibility that the peptide portion of from proline at the 315th position to glycine at the 328th position is forming a loop, providing a structure highly sensitive to proteases. That is, CD14 proteins are digested at this portion and the proteins released into blood are low molecular weight soluble CD14 proteins.

A typical amino acid sequence of high molecular weight soluble CD14 protein is shown in SEQ ID No. 1. That is, an antibody according to the first embodiment of the present invention is preferably an antibody that binds to the C-terminus of this sequence and more preferably an antibody that binds to any of the C-terminal 41 amino acids portion. Further, preferably the antibody of the first embodiment of the present invention does not bind to portions other than the C-terminal 41 amino acids portion. The amino acid sequence of the 316th to the 328th positions or the amino acid sequence of the 331st to the 345th positions described in SEQ ID No. 1 is an amino acid sequence that exists in the high molecular weight soluble CD14 protein but does not exist in the low molecular weight soluble CD14 protein. Further, an antibody to the polypeptide having an amino acid sequence of the 316th to the 356th positions described in SEQ ID No. 1 is included in the antibody of the present invention. Furthermore, an antibody to a polypeptide having an amino acid sequence of from the 316th to the 328th positions or an antibody to a polypeptide having an amino acid sequence of from the 331st to the 345th positions described in SEQ ID No. 1 is also included in the antibody of the present invention.

Figure 2:
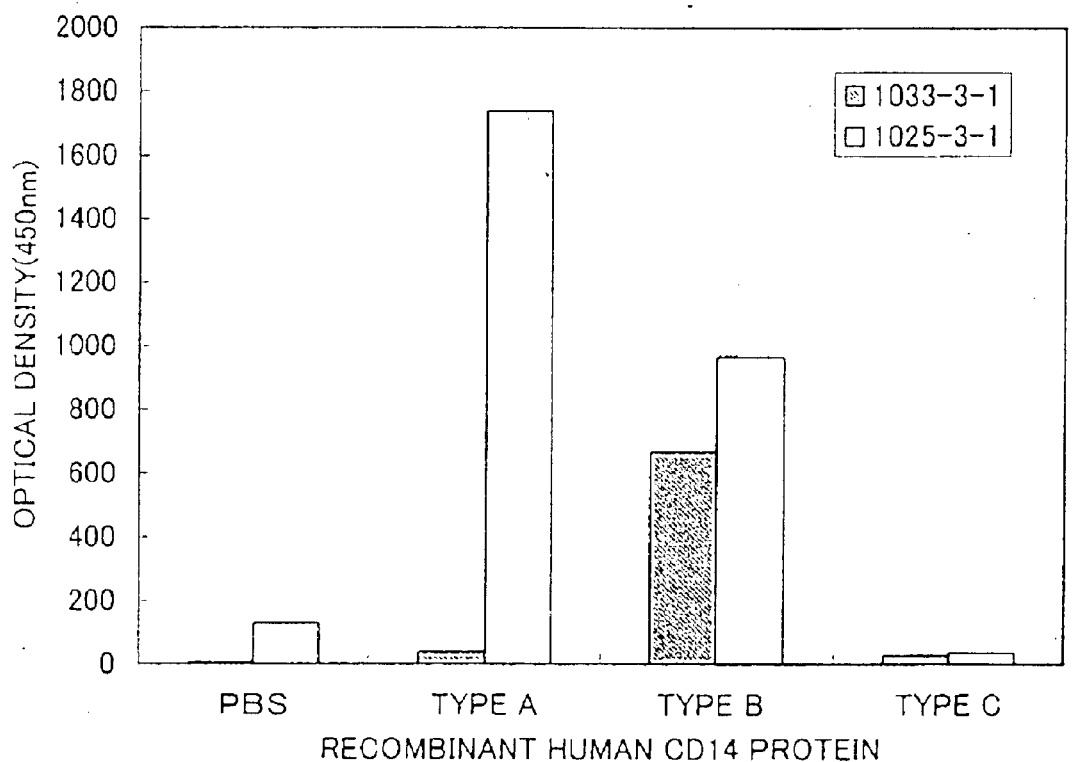
FIG. 2 is a diagram illustrating results of measurement of the specificity of monoclonal antibodies (F1033-3-1 and F1025-3-1) by an ELISA method based on the reactivity with recombinant human CD14 proteins. PBS, Type A, Type B and Type C indicate reactivities with no antigen, high molecular weight soluble CD14 protein of the type that has a length of the full length minus 28 amino acids, high molecular full length soluble CD14 protein, and high molecular weight soluble CD14 protein of the type that has a length of the full length minus 41 amino acids, respectively.

From the results shown in FIG. 2, it can be seen that an antibody that recognizes amino acids 316 to 328 described in SEQ ID No. 1 or a portion thereof also recognizes shorter soluble CD14 proteins in the high molecular ones so that it is suitable for separate the of molecule species. On the other hand, an antibody that recognizes amino acids 331 to 345 described in SEQ ID No. 1 or a portion thereof is suitable for separating only the high molecular full length soluble CD14 protein.

The antibody of the present invention may be either a polyclonal antibody or a monoclonal antibody. To specifically detect a high molecular weight soluble CD14 protein, it is desirable to use antibodies to certain limited epitopes and hence monoclonal antibodies are preferable. Molecule species are not particularly limited. Immunoglobulins of any class, subclass or isotype may be used. Fragments of an antibody may be included in the present invention as far as they bind to a high molecular weight soluble CD14 protein but do not bind to a low molecular weight soluble CD14 protein.

The antibodies of the present invention can be prepared using a known technology. For example, monoclonal antibodies can be prepared by the following method. Immunocytes of a mammal immunized with a polypeptide having all or a portion of the amino acid sequence shown in SEQ ID No. 1 as an immunogen are fused with myeloma cell lines to prepare hybridomas, from which a clone is selected that binds to a high molecular weight soluble CD14 protein but does not bind to a low molecular weight soluble CD14 protein, whereby an antibody is prepared.

The polypeptide may be prepared by using a commercially available peptide synthesizer. The mammal to be immunized is not particularly limited. However, it is preferable to select it taking into consideration compatibility with the myeloma cell line to be used for fusion. Mouse, rat, hamster or the like is preferred. As the myeloma cell line, various known cell lines can be used. They include myeloma cell lines such as P3, P3U1, SP2/O, NS-1, YB2/0 and Y3-Agl, 2, or 3. The immunization can be performed by a known method. For example, immunization is performed by administering an antigen intraperitoneally, subcutaneously, intravenously or into the foot pad. The antigen may be administered in combination with an adjuvant and it is preferable to administer the antigen in a plurality of times. The immunocyte is preferably a spleen cell or a cell derived from lymph node isolated several days, for example, 3 days after the final administration of the antigen. The fusion of immunocytes and myeloma cell lines can be performed using a known method such as the method of Milstein et al. (Methods in Enzymol., Vol. 73, p. 3). For example, mention may be made of the method using polyethylene glycol (PEG) as a fusing agent, an electric field-induced cell fusion method, or the like. The mixing ratio of immunocyte and myeloma cell lines is not particularly limited as far as it allows the fusion. However, it is preferable to make the amount of myeloma cell lines 1/10 to the equivalent relative to immunocyte. In the method in which cell fusion is performed using PEG (mean molecular weight: 1,000 to 4,000), the concentration of PEG is not particularly limited. However, it is preferable that fusion is performed at a concentration of 50%. An auxiliary such as dimethyl sulfoxide may be added as an enhancer of the fusion efficiency. The fusion is started by addition of a PEG solution warmed at 37° C. to mixed cells and is terminated by addition of a culture medium after 1 to 5 minutes' reaction. The hybridomas created by the fusion are incubated for 1 to 7 days in a selective enrichment medium such as a culture medium containing hypoxanthine, thymidine, and aminopterine (HAT medium) to separate them from nonfused cells. The obtained hybridomas are further selected by antibodies produced by them. The selected hybridomas are converted into a monoclonal by a known limiting dilution method to establish a monoclonal antibody producing hybridoma. As the method for detecting the activity of the antibody that the hybridoma produces, a known method may be used. For example, mention may be made of an ELISA, an agglutination reaction, and a radio immunoassay. The established hybridoma may be cultivated by a known method and a monoclonal antibody may be obtained from the culture supernatant. The hybridoma is administered to a mammal having compatibility therewith to allow proliferation, and the proliferated hybridoma is obtained from the ascites. Purification of the antigen can be performed using a known purification means such as a salting out, a gel filtration, an ion exchange chromatography, or an affinity chromatography.

Preferred examples of the antibody of the present invention include F1033-3-1 antibody produced by hybridoma F1033-3-1 or antibody F1025-3-1 produced by hybridoma F1025-3-1, the hybridomas being obtained by fusion between immunocytes obtained by immunizing a rat with 13 to 15 amino acids peptide selected from a high molecular weight soluble CD14 protein as an antigen and myeloma cell lines.

A second embodiment of the present invention relates to a polypeptide consisting of consecutive 6 to 41 amino acids in an amino acid sequence consisting of 41 amino acids of the 316th to the 356th positions of the amino acid sequence described in SEQ ID No. 1.

As described above, the antibody according to the first embodiment of the present invention preferably binds to any of the portion of 41 amino acids from the C-terminus from the 356 amino acid residues described in SEQ ID No. 1, that is, glycine at the 316th position to alanine at the 356th position, but does not bind to portions other than the above 41 amino acids portion. Therefore, there is the possibility that polypeptides having any part of the 41 amino acids portion can be used for determining the antibody of the first embodiment. However, for polypeptides to express a higher dimensional structure, 6 or more amino acid residues are necessary.

Therefore, the polypeptide according to the second embodiment of the present invention consisting of any consecutive 6 to 41 amino acids out of the sequence consisting of 41 amino acids from glycine at the 316th position to alanine at the 356th position of the amino acid sequence described in SEQ ID No. 1 has the possibility that it may serve as an antigen or epitope for the antibody of the first embodiment. Such a polypeptide can be used as an antigen or epitope for F1025-3-1 antibody shown in examples described later if it consists of, for example, an amino acid sequence of from the 316th to the 328th positions described in SEQ ID No. 1. Also, if it consists of an amino acid sequence of the 331st to the 345th positions described in SEQ ID No. 1, it can be used as an antigen or epitope of F1033-3-1 antibody shown in examples described later. The polypeptide of the present invention can be made by a known method and prepared using a commercially available peptide synthesizer.

A third embodiment of the present invention relates to a hybridoma that produces F1033-3-1 antibody or F1025-3-1 antibody, which is a preferred example of the first embodiment of the present invention.

The hybridomas of the present invention can be prepared by the method described in the first embodiment of the present invention.

Preferred examples of the hybridomas of the present invention include hybridomas deposited at Bio Engineering and Industrial Technology Laboratory, Institute of Industrial Science and Technology at 1–3, Higashi 1-chome, Tsukuba-shi, Ibaragi-ken, Japan on Feb. 9, 1999 (Accession No. P-17209) and Mar. 30, 1999 (Accession No. P-17350), transferred from the original deposits to international deposits on Sep. 11, 2000 under Accession No. FERM BP-7295 and Accession No. FERM BP-7296, respectively.

A fourth embodiment of the present invention relates to a measurement method for specifically determining the quality or quantity of a high molecular weight soluble CD14 protein, characterized in comprising using the antibody according to the first embodiment of the present invention.

Using the antibody according to the first embodiment of the present invention that binds to a high molecular weight soluble CD14 protein but does not bind to a low molecular weight soluble CD14 protein, a high molecular weight soluble CD14 protein in a sample can be qualitatively or quantitatively determined separately from other low molecular weight soluble CD14 proteins with high sensitivity, simply and easily, and specifically. A typical polypeptide of the high molecular weight soluble CD14 protein is a polypeptide consisting of amino acid sequence described in SEQ ID No. 1.

The principle of detection of a substance to be tested by the measurement method of the present invention is not particularly limited. However, an agglutination method, a sandwich method, a solid phase direct method or a solid phase binding method, a competitive method and the like are exemplified. Among them, the sandwich method and competitive method are preferred. The sandwich method is particularly preferred.

In the agglutination method, an antibody is bound to the surface of latex particles or erythrocytes (for example, sheep erythrocytes) to cause agglutination of particles when a specimen is present and the degree of agglutination is used as an index in order to qualitatively or quantitatively determine a high molecular weight soluble CD14 protein specifically.

In this agglutination method, particles that are generally used, such as particles of gelatin, micro bead, carbon, etc. can be employed in addition to latexes and erythrocytes.

In the sandwich method, solid phase direct method, solid phase binding method, or competitive method, measurement can be performed using labeled antibodies or antigens and is based on the principle of enzyme immunoassay (EIA), radio immunoassay (RIA), Chemiluminescence immunoassay, fluoroimmunoassay, time-resolved fluoroimmunoassay (TR-FIA), immuno chromatography assay (ICA) or the like.

In the solid phase direct method, a specimen (sample) is directly adsorbed on a solid phase and the high molecular CD14 protein non-adsorbed surface of the solid phase is subjected to blocking with a protein that does not affect the measurement system, for example, BSA (bovine serum albumin) and then an enzyme-labeled antibody that recognizes the high molecular weight soluble CD14 protein is added for reaction. Subsequently, the same operation as in the sandwich method is performed to qualitatively or quantitatively determine the high molecular weight soluble CD14 protein in the specimen with specificity.

In the competitive method, a certain amount of high molecular weight soluble CD14 protein that the antibody to be used recognizes is directly adsorbed on a solid phase and subjected to blocking. Thereafter, an enzyme labeled antibody that recognizes the high molecular weight soluble CD14 protein and specimen (sample) are added thereto. After allowing reaction for a certain time, the reaction mixture is washed to remove substances that do not bind to the solid phase and then a coloring substrate is added for reaction with the enzyme. By measuring the degree of inhibition of binding of the enzyme-labeled antibody to the solid phase high molecular weight soluble CD14 protein by the addition of the specimen, the high molecular weight soluble CD14 protein in the specimen is qualitatively or quantitatively determined with specificity.

Note that the high molecular weight soluble CD14 protein in the specimen may be qualitatively or quantitatively determined with specificity by firstly adsorbing the antibody onto the solid phase, adding the high molecular weight soluble CD14 protein labeled with the enzyme simultaneously with the specimen and then measuring the degree of inhibition of the binding of the labeled product to the solid phase antibody by addition of the specimen.

As a method other than those described above, there is also a method in which antigen antibody reaction is performed in a liquid phase, thereafter high molecular weight soluble CD14 protein bound with a labeled antibody is separated, whereby qualitatively or quantitatively determining the high molecular weight soluble CD14 protein with specificity. Also, a high molecular weight soluble CD14 protein can be qualitatively or quantitatively determined with specificity not by labeling an antibody that recognizes a high molecular weight soluble CD14 protein but obtaining a secondary antibody that recognizes the above antibody, labeling it, and performing antigen antibody reaction.

The measurement method according to the fourth embodiment of the present invention can be used also for the purpose of selectively determining the quantity of a specified soluble CDI4 protein form high molecular weight soluble CD14 proteins. For example, by using F1025-3-1 antibody and F1033-3-1 antibody shown in examples described later and subtracting the measured amount of the amino acid sequence of the 331st to the 356th positions of the soluble CD14 protein obtained with F1033-3-1 antibody from the measured amount of the amino acid sequence of from the 316th to the 356th positions of the soluble CD14 protein obtained with the F1025-3-1 antibody, the amino acid sequence of from the 316th to the 331st positions of soluble CD14 protein can be quantitatively determined fractionally. Major soluble CD14 proteins corresponding to these amino acid sequences include a soluble CD14 49 kDa protein and a soluble CD14 55 kDa protein, and a soluble cD14 55 kDa protein, and a soluble CD14 49 kDa protein, respectively.

Furthermore, using the measurement method according to the fourth embodiment of the present invention, a diagnostic reagent or kit for diseases associated with a high molecular weight soluble CD14 protein, comprising the antibody according to the first embodiment of the present invention can be prepared. The antibody according to the first embodiment of the present invention is essential as a constituent of the diagnostic reagent or kit. However, other than that, components therein are not particularly limited as far as they do not interfere with the results of the above-described measurements.

A fifth embodiment of the present invention relates to a measurement method for obtaining the amount of a low molecular weight soluble CD14 protein in a body fluid. The measurement method is not particularly limited as far as it can measure the amount of a low molecular weight soluble CD14 protein. For example, it may include a method of subtracting the amount of a high molecular weight soluble CD14 protein in the body fluid from the total amount of soluble CD14 proteins in the body fluid, a method of extracting soluble CD14 proteins from the body fluid, removing a high molecular weight soluble CD14 protein from the extract and measuring the amount of protein in the resulting liquid, a method of isolating soluble CD14 proteins in the body fluid by electrophoresis, HPLC, MS or the like and quantitatively determining the low molecular weight soluble CD14 protein, and the like. It is preferable that in these exemplified methods, the antibody according to the first embodiment of the present invention be used to perform the methods simply and easily. Further, a method of measuring a low molecular weight soluble CD14 protein using the measurement method according to the fourth embodiment of the present invention is preferred.

The measurement method for a low molecular weight soluble CD14 protein according to the present invention comprises the steps of measuring the total amount of soluble CD14 proteins in the specimen, measuring the amount of high molecular weight soluble CD14 proteins by a system for specifically measuring high molecular weight soluble CD14 proteins, and subtracting from the total amount of soluble CD14 proteins the amount of high molecular weight soluble CD14 proteins. The step of measuring the total amount of soluble CD14 proteins present in the specimen can be performed by the known method described herein. For example, the total amount of soluble CD14 proteins is measured by using an antibody that binds to all the soluble CD14 proteins such as 3C10, MEM-18, 28C5, or 23G4 described in BACKGROUND ART. Also, other substances that recognize soluble CD14 proteins, more specifically, receptors such as 2PS and 2BP may be used to detect soluble CD14 proteins and the total amount thereof may be measured.

The step of measuring the amount of high molecular weight soluble CD14 proteins by a system for specifically measuring high molecular weight soluble CD14 proteins can be performed by the measurement method according to the fourth embodiment of the present invention.

By subtracting from the total amount of soluble CD14 proteins the amount of high molecular weight soluble CD14 proteins, the amount of all the soluble CD14 proteins in the specimen except the high molecular weight soluble CD14 protein can be obtained. Here, all the soluble CD14 proteins except for the high molecular weight soluble CD14 protein correspond to the low molecular weight soluble CD14 protein. Therefore, the low molecular weight soluble CD14 protein in a specimen can be quantitatively determined separately by the above procedure. In the above-described procedure, if measurement kits and measurement conditions for high molecular weight soluble CD14 protein and soluble CD14 proteins are different when quantitatively and separately determining the low molecular weight soluble CD14 protein, each measured values can be corrected using standards of CD14 proteins included in the above-described measurement kits.

The low molecular weight soluble CD14 protein measured by the measurement method of the present invention comprises mainly a soluble CD14 36 kDa protein. However, besides the 36 kDa band indicating the soluble CD14 36 kDa protein, a plurality of bands are confirmed between 7.7 to 42 kDa in the analysis of human urine as shown in Example 12 and hence the low molecular weight soluble CD14 protein also includes those proteins corresponding to these bands.

The present invention also includes diagnostic reagent or kit for diseases associated with a low molecular weight soluble CD14 protein by quantitatively determining the low molecular weight soluble CD14 protein. The diagnostic reagent or kit of the present invention is characterized in that the measurement method according to the fifth embodiment of the present invention is included as a step for performing the measurement. In particular, where the specimen is blood, it is characterized by measuring a soluble CD14 36 kDa protein. As the disease associated with a low molecular weight soluble CD14 protein, sepsis is exemplified.

Preferred examples of the diagnostic reagent or kit of the present invention include a diagnostic reagent or kit that comprises the antibody according to the first embodiment of the present invention for isolating or measuring only the high molecular weight soluble CD14 protein and a substance for measuring all the soluble CD14 proteins. The substance for measuring all the soluble CD14 proteins includes an antibody that recognizes the N-terminus of CD14 proteins, LPS-like substance that binds to CD14 or LPS-binding protein (LBP) and the like. For these, known antibodies and the like may be used.

Other constituents are not particularly limited as far as they do not interfere with the results of the above-described measurement.

A diagnostic reagent or kit is exemplified that contains as optional constituents, a solid phase for immobilizing an anti-CD14 antibody by adsorption, chemical bond or the like, a labeled antibody, buffer solution for the specimen or labeled antibody, a substrate and coloring agent suitable for an enzyme where the labeled antibody uses the enzyme, a blocking agent, a washing agent, a stopping agent and the like.

The solid phase includes micro titer plate, plastic bead, magnetic particles or membrane, and the like.

The labeled antibody includes antibodies labeled with an enzyme label such as peroxidase, oxidase, alkaline phosphatase, urokinase, or β-galactosidase, a chemiluminescence label such as acridinium or aequorin, or a fluorolabel such as FITC (fluorescein isothiocyanate).

The substrate for the enzyme (coloring agent) includes tetra methyl benzidine or the like for peroxidase, and p-nitrophenyl phosphate or the like for alkaline phosphatase.

A sixth embodiment of the present invention relates to a method for diagnose the sepsis using the measurement method according to the fifth embodiment of the present invention.

As described above, the present inventors confirmed that in patients suffering from sepsis, low molecular weight soluble CD14 protein increases. The method for diagnosing sepsis according to the present invention is based on this finding and is practiced by obtaining the amount of the low molecular weight soluble CD14 protein in the blood of recipient by the measurement method according to the fifth embodiment of the present invention, and comparing this value with the value or range of value of normal persons standardized by taking a mean value of measurement results on normal persons or otherwise. For example, a mean value of normal persons +2SD or 3SD is used as a cutoff value and the case where the value of CD14 protein is higher than the cutoff value is judged to be positive and so on. Also, it is preferable that the diagnostic method be performed by comparing standardized values of the values or ranges of value of low molecular weight soluble CD14 protein concentrations preliminarily obtained for normal persons and patients suffering from sepsis with the measured values of respective individuals. For example, assuming the value of low molecular weight soluble CD14 protein for normal persons is 0 to 1.1 μg/ml and the value for patients suffering from sepsis is 2.3 to 6 (μg/ml), and comparing measured values with these values. The method for diagnose the sepsis according to the present invention will be concretely exemplified in Example 11.

Furthermore, the sixth embodiment relates to a method for diagnosing sepsis. The measurement methods according to the fourth and fifth embodiments of the present invention can be used in the diagnosis of diseases associated with other CD14 proteins. Diseases associated with such soluble CD14 proteins include diseases associated with high molecular weight soluble CD14 protein, diseases associated with low molecular weight soluble CD14 protein or diseases associated with all the CD14 proteins. These diseases include rheumatic arthritis, AIDS, autoimmune diseases, hemolytic anemia, tumors, atopic diseases, allergy diseases, sarcoidosis, malaria, and psoriasis.

The diagnosis is performed by measuring concentrations of high molecular weight soluble CD14 protein, other soluble CD14 protein and all the CD14 proteins in the serum, urine or body fluid, or in culture supernatant of patients suffering from diseases associated with CD14 proteins using the measurement method of the present invention, obtaining the amount of the low molecular weight soluble CD14 protein from these measured values, and comparing it with a standardized value or range of value for normal persons obtained by taking a mean value of measured results on normal persons or otherwise. The comparison was specifically indicated with respect to the method for diagnosing sepsis. It is preferable that the diagnosis be performed by comparing values of concentrations of high molecular weight soluble CD14 protein, low molecular weight soluble CD14 protein and all the CD14 proteins or standardized values thereof preliminarily obtained depending on disease or clinical symptom with measured values of CD14 proteins for respective individuals.

Further, diagnosis may be performed based on the results obtained by quantitative determination of a specified CD14 protein from the high molecular weight soluble CD14 proteins described above in the measurement method according to the fourth embodiment of the present invention.

As another example, by quantitative determination of a 49 kDa CD14 protein using high molecular CD14 protein specific antibodies, F1025-3-1 antibody and F1033-3-1 antibody, that the present inventors prepared, the relationship between the above quantitatively determined values and the above-described CD14 protein associated diseases can be confirmed.

EXAMPLES

Hereinafter, the present invention will be described more concretely with examples. However, the examples are only exemplary and the present invention should by no means be construed as being limited thereto. Further, symbols used in the following description are based on the symbols as a convention in the art. The numbers of amino acids in the amino acid sequences are those described in SEQ ID No. 1 in the Sequence Listing.

Example 1

Preparation of a Peptide Specific to a High Molecular Weight Soluble CD14 Protein Using an amino acid sequence search software DNASIS (Hatachi Software Engineering), homology search of human CD14 protein sequence, monkey CD14 protein sequence, mouse CD14 protein sequence, and rat CD14 protein sequence were performed. As a result, the homology of human/monkey was 94%, that of human/mouse was 65%, and that of human/rat was 63%. Next, to prepare an antibody having specificity to a high molecular weight soluble CD14 protein, homology search was performed on the sequence of from glycine at the 316th position to alanine at the 356th position (hereinafter described as C-terminal amino acid) of the sequence described in SEQ ID No. 1. As a result, the homology of human/mouse was 44% and that of human/rat was 46%. Because the homology in this region was 44 to 46%, it was expected that mouse and rat could be caused to produce a specific antibody to this region and the following analysis was performed. Analysis performed using a secondary structure prediction program by Chou-Fasman and Robson indicated that the sequence of from the 316th to the 328th positions of the C-terminal 41 amino acids is of a coil structure and this suggested that the sequence could be an excellent epitope in preparing an antibody. Further, the results indicated the sequence of from the 331st to the 345th positions had a ratio of hydrophobic amino acids as high as 69%. However, structurally, it was expected that the sequence takes a combination structure having a partial turn structure in a β-structure, so that considering that under certain conditions the sequence is exposed on the surface of the protein, it was judged that immunization is possible. From these, the sequence of from the 316th to the 328th positions and that of the 331st to the 345th positions of the sequence described in SEQ ID No. 1 were selected as peptides specific to high molecular weight soluble CD14 protein to be used for immunization (hereinafter, described as peptide 13 and peptide 15, respectively).

To bind the selected peptides with a carrier protein at the C-terminus thereof through a SH group, cystein was inserted into the C-terminus. The synthesis of peptide was performed using ABI432A peptide synthesizer (Applied). The peptide was cut out from the resin by a conventional procedure and purified by C18 reverse phase HPLC (CAPCELL-PAK, Shiseido Corp.).

Example 2

Preparation of a Peptide Carrier Antigen using a Synthetic Peotide

The peptide prepared in Example 1 was dissolved in distilled water to 10 mg/ml and mixed with 10 mg/ml of maleimide activated key hole limpet hemocyanine (KLH, PIERCE) in equal amounts. After 2 hours' reaction at room temperature, the reaction mixture was desalted by NAP-10 column (Pharmacia) to obtain peptide 13 carrier antigen (hereinafter, described as peptide 13-KLH) and peptide 15 carrier antigen (hereinafter, described as peptide 15-KLH). The concentration of proteins obtained by dividing the amount of used KLH by the amount of liquid was used.

Example 3

Construction of a Plasmid Expressing Recombinant Human CD14 Protein (1) Construction of a Plasmid Expressing Human CD14 Protein in a Mammmal Cell To express human CD14 proteins in a mammal cell, expression plasmid (pM1650) was constructed. That is, gene fragments obtained by cleaving pUCHl4P-4 described in International Patent Laying-open Publication WO98/39438 with XbaI and HindIII were inserted into the XbaI/HindIII site of pcDNA3.1(−) (Invitrogen Co.) by a conventional procedure and Escherichia coli JM109 (TaKaRa Shuzo) was transformed with the inserted product and then cloned by a conventional procedure to obtain pM1650.

(2) Construction of a Plasmid Expressing Soluble Human CD14 Proteins in a Mammal Cell To express a soluble human CD14 protein that has a C-terminus by 28 amino acids shorter than the amino acid sequence described in SEQ ID No. 1 and a soluble human CD14 protein having the amino acid sequence described in SEQ ID No. 1 in a mammal cell, there were constructed an expression plasmid (pml653) obtained by replacing the sequence encoding valine at the 329th position of the human high molecular weight soluble CD14 protein shown in SEQ ID No. 1 by a translation stop codon sequence and an expression plasmid (pM1656) obtained by replacing the sequences encoding asparagine at the 326th position and glycine at the 328th position of the human high molecular weight soluble CD14 protein shown in SEQ ID No. 1 by a sequence encoding glutamine and a sequence encoding valine, respectively, so as to be secreted in full length directly in a culture supernatant without GPI anchoring.

Using the above-described pUCHl4P-4 as a template, sense primer: H0176S (CACGCCAGAACCTTGTGAGC) (SEQ ID No. 2) and antisense primer: H1148A-49k (GTCAGTGCACAGGCTGGGACCACAACGGATTGCA-TTGA) (SEQ ID No. 3) or sense primer: H0176S and antisense primer: H1140A-M3 (GTCAGTGCACA-GGCTGGGACCACAACGGATTGCATTGA) (SEQ ID No. 4) were mixed followed by 30 cycles of PCR reaction at 94° C. for 30 seconds, at 55° C. for 30 seconds, and at 72° C. for 1 minute using Ex Taq polymerase (TaKaRa Shuzo) to obtain DNA fragments. The DNA fragments were digested with XhoI and ApaLI, respectively, and ligated with the DNA fragment (about 5.8 kb) obtained by digestion with XhoI and HindIII and the DNA fragment (about 0.2 kb) obtained by digestion thereof with ApaLI and HindIII. Then Escherichia coli JM109 (TaKaRa Shuzo) was transformed with these ligation reaction mixtures and pM1653 and pM1656 were cloned by a conventional procedure.

Next, to express a soluble human CD14 protein of the type that has a sequence by 41 amino acids shorter than the sequence described in SEQ ID No. 1 in a mammal cell, an expression plasmid (pM1657) in which a translation stop codon was inserted after the sequence encoding proline at the 315th position was prepared. That is, antisense primer: Hl1101A-Hind (CCCAAGCTTCTATTAGAGATCG-AGCACTCT) (SEQ ID No. 5) obtained by binding a translation stop codon (TAA, TAG) and HindIII site (AAGCTT) to the sequence encoding 5 amino acids of from proline at the 311th position to proline at the 315th position was designed and then using sense primer: H0176S and pUCH14-P as templates, PCR reaction at 94° C. for 30 seconds, at 55° C. for 30 seconds and at 72° C. for 1 minute was repeated for 30 cycles using Ex Taq polymerase (TaKaRa Shuzo) to obtain a DNA fragment. The DNA fragment was digested with XhoI and HindIII, respectively. The product was ligated with a DNA fragment (about 5.8 kb) obtained by digestion of pMl650 with XhoI and HindIII. Then, Escherichia coli JM109 cells were transformed with the ligation reaction mixture and pM1657 was cloned.

Example 4

Preparation of recombinant human CD14 protein

Recombinant human CD14 proteins were prepared by DEAE-dextran method using plasmids (pM1650, pM1653, and pM1656). That is, COS-1 cells (ATCC CRL1650) were cultivated and transfected at a stage where cell concentration was 70% confluent. The transfection was performed according to the method described in Transfection GUIDE by Promega Co. and 6 μg of DNA per 60 mm culture plate was used. The recombinant human CD14 proteins were produced by replacing the medium on the day next to the day of transfection by a DMEM medium containing 1% calf fetus serum and incubating at 37° C. for 72 hours. The culture supernatant was recovered and centrifuged at 3000 rpm and thereafter fine particles were removed through a 0.45 μm membrane.

The recombinant human CD14 protein was purified using an affinity column prepared by binding anti-CD14 protein monoclonal antibody 3C10 (prepared from ATCC228-TIB hybridoma obtained from American Type Culture Collection) created by Steinman et al. to HiTrap NHS-activated column (Pharmacia) in an amount of 5 mg per 1 ml of resin. First the column was equilibrated with 0.1 M phosphate buffer (pH 7.4) and the recovered culture supernatant was applied thereto. After the application, the column was washed with 0.1 M phosphate buffer (pH 7.4) and then the bound recombinant human CD14 protein was eluted with 0.1 M glycine hydrochloric acid buffer (pH 2.5). After rendering the pH of the eluate back to near neutrality, the eluate was freeze-dried. Then, this was dissolved in distilled water, dialyzed against 0.076 M phosphate buffer (pH 6.4) to obtain purified recombinant human CD14 protein. The concentration of protein was measured by a Lowry method using BSA as a standard.

Example 5

Creation of Monoclonal Antibody Specific to High Molecular Weight Soluble CD14 Protein (1) Generation of Hybridoma Producing Anti-CD14 Protein Monoclonal Antibody (1)-1 Production of Rat Monoclonal Antibody 100 μg of peptide 13-KLH or peptide 15-KLH was dissolved in 100 μl of physiological saline and mixed with Freund's complete adjuvant (DIFCO) in equivalent amounts and the mixture was administered to each rear foot pad of an 8-week aged female Wistar rat in an amount of 100 μl. After 2 weeks, ilium bone lymph node was extirpated and fusion was performed. That is, lymphocytes were separated from the lymph node using a cell strainer (Falcon) and mixed with myeloma cells (Sp2/O—Ag14), followed by cell fusion according to Tamie Ando and Takeshi Chiba "Introduction to Monoclonal Antibody Experimental Operations," p. 83, 1991 (Kodansha) using polyethylene glycol. Hybridomas were selected using an HAT medium and after 1 week, hybridomas producing the target antibody were screened.

The screening was performed by an ELISA method in which peptide 15 was directly immobilized on a plate. First, 50 μl per well of Sulfo-SMCC (PIERCE) diluted with 0.1 M phosphate buffer (pH 7.4) to 0.1 mg/ml was added to Aminoplate (white in color, Sumitomo Bakelite) and left to stand at room temperature for 1 hour. Then the plate was washed with deionized water 5 times and thereafter peptide 15 diluted with 0.1 M phosphate buffer (pH 7.4) to 5 μg/ml was added to each well in an amount of 50 μl and allowed to react at 37° C. for 1 hour. After completion of the reaction, the plate was washed with deionized water 5 times and 100 μl of 0.076 M phosphate buffer (pH 6.4) (hereafter, described as PBS) containing 4 mg/ml cysteamine, 20% Blockace (Snow Brand Milk Mfg), and 0.1% Tween 20 was added to each well and left to stand at room temperature for 1 hour to effect blocking. After adding the culture supernatant sampled form the obtained hybridomas to each well and allowing it to react at 37° C. for 1 hour, the plate was washed 3 times with physiological saline containing 0.05% Tween 20. Then, 50 μl of a solution obtained by diluting 1000-fold peroxidase labeled anti-rat immunoglobulins antibody (DAKO) with PBS containing 10% rabbit serum was added to each well. After reaction at 37° C. for 1 hour, the plate was washed 5 times in the same manner as above and a tetramethylbenzidine solution containing 0.01% hydrogen peroxide was added to each well. After 10 minutes' reaction at room temperature, the reaction was stopped with a 0.5 M sulfuric acid solution. Based on the results, 11 wells that contain hybridomas producing an antibody that reacts with peptide 15 were selected. Then, it was confirmed as to whether or not the selected wells react with recombinant human CD14 proteins. First, the recombinant human CD14 protein purified in Example 3 was diluted with 0.01 M carbonate buffer (pH 9.5) to 1 μg/ml and 50 μl thereof was added to each well of Immunoplate (Maxisorb, NUNC). After 1 hour's reaction at 37° C., the plate was washed with deionized water 5 times and 100 μl of PBS containing 0.5% BSA was added to each well to effect blocking. Then, the culture supernatant sampled from the selected hybridomas was added to each well and allowed to react at 37° C. for.1 hour. Thereafter, the plate was washed 3 times with physiological saline containing 0.05% Tween 20. 50 μl of a solution obtained by diluting peroxidase labeled anti-rat immunoglobulins antibody (DAKO) with PBS containing 10% rabbit serum 1000-fold was added to each well. After reaction at 37° C. for 1 hour, the plate was washed 5 times in the same manner as above and a tetramethylbenzidine solution containing 0.01% hydrogen peroxide was added to each well. After 10 minutes' reaction at room temperature, the reaction was stopped with a 0.5 M sulfuric acid solution and optical density at 450 nm was measured using a plate spectrophotometer (NJ-2100, Japan Intermed). As a result, a well (F1033-3) containing hybridoma that reacted with a high molecular weight soluble CD14 protein was selected and cloned by a limiting dilution method. After 10 days, screening was performed using the reactivity with peptide 15-KLH as an index. That is, 50 μl/well of each of solutions of KLH and of peptide 15-KLH prepared in Example 2, each diluted with PBS to 0.2 μg/ml was added to Immunoplate (Maxisorb, NUNC) and allowed to react at 45° C. for 30 minutes to immobilize the antigens. After washing the plate 5 times with deionized water, 100 μl of PBS containing 0.5% BSA was added to each well to effect blocking. The culture supernatant of hybridoma after the cloning was added to each well and after reaction at room temperature for 1 hour, the plate was washed 3 times with physiological saline containing 0.05% Tween 20. Then, peroxidase labeled anti-rat immunoglobulins antibody (DAKO) was diluted 1000-fold with PBS containing 10% rabbit serum and added to each well in an amount of 50 μl. After 1 hour's reaction at room temperature, the plate was washed 5 times in the same manner as above and a tetramethylbenzidine solution containing 0.01% hydrogen peroxide was added to each well. After 10 minutes' reaction at room temperature, the reaction was stopped with a 0.5 M sulfuric acid solution. The optical density at 450 nm was measured using a plate spectrophotometer (NJ-2100, Japan Intermed). As a result, an antibody producing hybridoma was selected that does not react with KLH but reacts only with peptide 15-KLH. The selected hybridoma was cultivated in 10% FCS/RPMI-1640 medium (GIBCO) and then cultivated in Hybridoma-SFM medium (GIBCO) to produce an antibody. The antibody was purified using Prosep-G column (Bioprocessing). The subtype of the purified F1033-3-1 antibody was rat IgG2a.

Similarly, screening of hybridomas from a rat immunized with peptide 13-KLH was performed and an antibody producing hybridoma F1025-3-1 which binds to CD14 protein was established. The hybridoma was cultivated in Hybridoma-SFM medium (GIBCO) and purified in the same manner as above. The subtype of purified F1025-3-1 antibody was rat IgG1.

(1)-2 Preparation of HRP Labeled Antibody 0.5 g of peroxidase (Toyobo) was dissolved in distilled water, 100 mM periodic acid dissolved in distilled water was added thereto and the mixture was allowed to react at 25° C. for 20 minutes. After completion of the reaction, 1.5% ethylene glycol was added and after 10 minutes reaction at 25° C., the reaction mixture was dialyzed against 1 mM acetate buffer (pH 4.4). Purified F1033-3-1 antibody and F1025-3-1 antibody were dialyzed against 10 mM carbonate buffer (pH 9.5). 0.5 mg of peroxidase activated by addition of 1 M carbonate buffer (pH 9.5) to 0.5 mg thereof was mixed with each antibody in equivalent amounts and allowed to react at 25° C. for 2 hours. 4 mg/ml of sodium borohydride was added and reaction was further continued at 4° C. for additional 2 hours. The reaction mixture was dialyzed against PBS to obtain peroxidase labeled antibodies. The amount of liquid was measured and the concentration of antibody was calculated from the amount of antibody used.

(1)-3 Confirmation of the Specificity of Antibody

The specificity of the prepared monoclonal antibodies (F1033-3-1 and F1025-3-1) was confirmed. First, to confirm as to whether or not the antibody binds to the immunized peptide specifically, 50 µl/well of each of solutions of KLH, peptide 13-KLH, and peptide 15-KLH, each diluted with PBS to 0.2 µg/ml was added to Immunoplate (Maxisorb, NUNC) and allowed to react at 45° C. for 30 minutes to immobilize the antigens. Then, after washing the plate with deionized water, 100 µl of PBS containing 0.5% BSA was added to each well to effect blocking. Purified F1033-3-1 antibody and F1025-3-1 antibody were diluted with PBS to 1 µg/ml and added to each well each in an amount of 50 µl. After 1 hour's reaction at 37° C., the plate was washed 3 times with physiological saline containing 0.05% Tween 20. Then, 50 µl of a solution of peroxidase labeled anti-rat immunoglobulins antibody (DAKO) diluted 1000-fold with PBS containing 10% rabbit serum was added to each well. After 1 hour's reaction at 37° C., the plate was washed 5 times in the same manner as above and 50 µl of a tetramethylbenzidine solution containing 0.01% hydrogen peroxide was added to each well. After 10 minutes' reaction at room temperature, the reaction was stopped with a 0.5 M sulfuric acid solution. The optical density at 450 nm was measured using a plate spectrophotometer (NJ-2100, Japan Intermed). As shown in FIG. 1, F1033-3-1 antibody did not react with KLH or peptide 13-KLH but reacted only with peptide 15-KLH. From this it is apparent that this antibody reacts with peptide 15 specifically. Similarly, F1025-3-1 antibody did not react with KLH or peptide 15-KLH but reacted only with peptide 13-KLH, so that it was evidenced that the antibody reacts with peptide 13 specifically.

Next, using various recombinant human CD14 proteins, the specificity of F1033-3-1 antibody and F1025-3-1 antibody was studied. That is, soluble CD14 protein lacking C-terminal 28 amino acids (prepared from pM1653, hereinafter described as CD14 protein type A), full length high molecular weight soluble CD14 protein shown in SEQ ID No. 1 (prepared from pMl656, hereinafter described as CD14 protein type B), and soluble CD14 protein lacking C-terminal 41 amino acids (prepared from pM1657, hereinafter described as CD14 protein type C) were each diluted with PBS to 0.2 µg/ml and added to Immunoplate (Maxisorb, NUNC) in an amount of 50 µl/well. Reaction was performed at 37° C. for 1 hour to immobilize the recombinant human CD14 proteins. Then, after washing the plate with deionized water 5 times, 100 µl of PBS containing 0.5% BSA was added to each well to effect blocking. F1033-3-1 antibody and F1025-3-1 antibody were diluted with PBS to 1 µg/ml and added to each well in an amount of 50 µl. After 1 hour's reaction at 37° C., the plate was washed 3 times with physiological saline containing 0.05% Tween 20. Then, 50 µl of a solution of peroxidase labeled anti-rat immunoglobulin antibody (DAKO) diluted 1000-fold with PBS containing 10% rabbit serum was added to each well. After 1 hour's reaction at 37° C., the plate was washed 5 times in the same manner as above and 50 µl of a tetramethylbenzidine solution containing 0.01% hydrogen peroxide was added to each well. After 10 minutes' reaction at room temperature, the reaction was stopped with a 0.5 M sulfuric acid solution. The optical density at 450 nm was measured using a plate spectrophotometer (NJ-2100, Japan Intermed) . As shown in FIG. 2, F1025-3-1 antibody that recognizes high molecular weight soluble CD14 proteins type A and type B binds to the both but did not bind to low molecular weight soluble CD14 protein type C that has a sequence short of C-terminal 41 amino acids. On the other hand F1033-3-1 antibody bound only to type B high molecular weight soluble CD14 protein. From the above, it is clear that F1033-3-1 antibody specifically recognizes only type B high molecular weight soluble CD14 protein while F1025-3-1 antibody specifically recognizes only type A and type B high molecular weight soluble CD14 proteins.

Example 6

Epitope Analysis of F1033-3-1 Antibody and F1025-3-1 Antibody

To elucidate the amino acid sequence (hereinafter, described as epitope) in the high molecular weight soluble CD14 proteins that F1033-3-1 antibody and F1025-3-1 antibody prepared in Example 5 recognize, epitope mapping was performed using SPOTs system (CAMBRIDGE RESEARCH BIOCHEMICALS Co.). That is, according to the manual provided by CAMBRIDGE RESEARCH BIOCHEMICALS Co. and based on the amino acid sequence of CD14 protein (SEQ ID No. 1), various peptide chains were synthesized that have amino acid sequences consecutively dislocated by 2 amino acids between valine, the 246th amino acid and threonine, the 346th amino acid. As a result, 46 peptides of a length of 10 amino acids were synthesized on a membrane. After completion of the synthesis, the side chains of the peptide chains were deprotected and blocking was performed by the instructed method. Then, in a solution obtained by diluting F1033-3-l antibody or F1025-3-1 antibody with blocking buffer to 5 µg/ml, the membrane was allowed to react at room temperature for 6 hours. After completion of the reaction, the membrane was washed twice with T-TBS, and subsequently reacted with β-galactosidase labeled anti-rat IgG-F(ab')2 antibody (American Qualex Co.) diluted 500-fold with blocking buffer at 4° C. overnight. After discarding the reaction mixture, the membrane was washed twice with T-TBS and twice with PBS. Thereafter, a substrate for β-galactosidase was added and allowed to react at room temperature for about 30 minutes. Then, the membrane was washed twice with PBS to stop the reaction and the membrane was photographed. As a result, F1033-3-1 antibody was observed to show strong coloring in the 45th and 46th peptide chains as shown in Table 1 and it is apparent that the epitope sequence to be recognized is a sequence containing Ser Thr Leu Ser Val Gly Val Ser (SEQ ID No. 6), which is a sequence of from the 336th position to the 343rd position out of the sequence described in SEQ ID No. 1.

TABLE 1

| SPOT No. | Amino Acid Sequence | Intensity of Coloring |
|---|---|---|
| 44 | Ala Cys Ala Arg Ser Thr Leu Ser Val Gly (SEQ ID NO:8) | − |
| 45 | Ala Arg Ser Thr Leu Ser Val Gly Val Ser (SEQ ID NO:9) | ++ |
| 46 | Ser Thr Leu Ser Val Gly Val Ser Gly Thr (SEQ ID NO:10) | + |

The table above shows results of analysis of epitope that F1033-3-1 antibody recognizes in terms of intensity of coloring on the membrane by reactivity with peptide chains sythesized using SPOTs. The underlinings indicate a common sequence among the peptide chains that reacted.

F1025-3-1 antibody also shows strong coloring in the 35th to 37th peptide chains as shown in Table 2 and it was demonstrated that the epitope sequence it recognizes is a sequence containing Ala Leu Pro His Glu Gly (SEQ ID No. 7), which is a sequence of form the 318th position to the 323rd position out of the sequence described in SEQ ID No. 1.

TABLE 2

| SPOT No. | Amino Acid Sequence | Intensity of Coloring |
|---|---|---|
| 35 | Val Pro Gly THr Ala Leu Pro His Glu Gly (SEQ ID NO:11) | + |
| 36 | Gly THr Ala Leu Pro His Glu Gly Ser Met (SEQ ID NO:12) | ++ |
| 37 | Ala Leu Pro His Glu Gly Ser Met Asn Ser (SEQ ID NO:13) | + |

The table above shows results of analysis of epitope that F1025-3-1 antibody recognizes in terms of intensity of coloring on the membrane by reactivity with peptide chains synthesized using SPOTs. The underlinings indicate a common sequence among the peptide chains that reacted.

Example 7

Preparation of Anti-CD14 Protein Monoclonal Antibody

Using 3C10 affinity column prepared in Example 4, soluble CD14 proteins in sera of normal persons were purified and used as antigen to be immunized. The concentration of protein was determined by performing protein assay (BIO RAD) using BSA as a standard preparation, and concentrations were calculated.

Immunization was performed using rats and mice. For rats, 100 μl of antigen was administered to foot pad and for mice, 20 μg of antigen was administered to intraperitoneal route after mixing in equivalent amounts with Freund's complete adjuvant (DIFCO). For rats, cell fusion was performed by the method described in Example 5 after 2 weeks from the administration and hybridomas were selected using HAT medium. Then, using an ELISA method, antibody producing hybridomas were screened. That is, 50 μl of a solution of purified soluble CD14 protein diluted with 0.01 M carbonate buffer (pH 9.5) to 1 μg/ml was dispensed to each well of Immunoplate (Maxisorb, NUNC) and allowed to react at 37° C. for 1 hour to immobilize the antigen. Then, after washing the plate with deionized water 5 times, 100 μl of 0.5% BSA/PBS was added to effect blocking. After discarding the blocking liquid, 50 μl of the supernatant of hybridoma culture was added and allowed to react at 37° C. for 1 hour. Then, after washing the plate 3 times with physiological saline containing 0.05% Tween 20, 100 μl of a solution of peroxidase labeled anti-rat immunoglobulin antibody (DAKO) diluted 1000-fold with PBS containing 10% rabbit serum was added to each well. After 1 hour's reaction at 37° C., the plate was washed and 50 μl of a tetramethylbenzidine solution containing 0.01% hydrogen peroxide was added to each well. After 10 minutes, the reaction was stopped with a 0.5 M sulfuric acid solution and optical density at 450 nm was measured. Based on the results, hybridomas producing the antibodies that reacted with the immobilized soluble CD14 proteins were selected and cloned by a limiting dilution method. After 10 days, screening was performed in the same manner to obtain 25 kinds of anti-CD14 protein monoclonal antibodies.

For mice, after 2 weeks from the initial immunization, a solution of 20 μg of antigen dissolved in physiological saline was mixed with Freund's incomplete adjuvant (DIFCO) in equivalent amounts and the mixture was administered in the intraperitoneal route. After 1 week, an increase in antibody titer was confirmed by the above-described ELISA method. Final administration was performed by injecting 100 μg of antigen to the intraperitoneal route of mice. After 3 days, spleen was extirpated. From the spleen, lymphocytes were isolated and mixed with myeloma cell lines (P3×63-Ag. 8. U•1) in a ratio of 10:1 and fusion was performed using polyethylene glycol. Hybridomas were selected using HAT medium and after 1 week screening of hybridomas producing the target antibodies was performed by the above-described ELISA method. The hybridomas that reacted with the immobilized soluble CD14 proteins were cloned by a limiting dilution method and after 10 days screening was performed in the same manner to obtain 33 kinds of anti-CD14 protein monoclonal antibodies.

The obtained antibodies were cultivated by the method described in Example 5 and purified antibodies were prepared in the same manner.

Example 8

Development of Sandwich ELISA System (1) Search for Antibody that Enables Combination To search antibodies with which a sandwich ELISA can be prepared together with F1033-3-1 antibody and F1025-3-1 antibody, each of the purified antibodies prepared in Example 7 was diluted with PBS to 10 μg/ml and 50 μl of the solution was added to each well of Immunoplate (Maxisorb, NUNC) and allowed to react at 45° C. for 30 minutes to immobilize the antibodies. After washing the plate with deionized water, 100 μl of PBS containing 0.5% BSA was added to each well to effect blocking. After discarding the blocking liquid, then 50 μl of a solution of purified soluble CD14 protein diluted with 0.1% BSA/PBS to 100 ng/ml was added. As a blank, 0.1% BSA/PBS was used. After 1 hour's reaction at 25° C., the plate was washed 3 times with physiological saline containing 0.05% Tween 20. Then, peroxidase labeled F1033-3-1 antibody or peroxidase labeled F1025-3-1 antibody was diluted with PBS containing 10% rabbit serum to 1 μl/ml and added to each well in an amount of 50 μl. After 1 hour's reaction at 37° C., the plate was washed 5 times in the same manner as above and a tetramethylbenzidine solution containing 0.01% hydrogen peroxide was added to each well. After 10 minutes' reaction at room temperature, the reaction was stopped with a 0.5 M sulfuric acid solution. The optical density at 450 nm was measured using a plate spectrophotometer (NJ-2100, Japan Intermed). As a result, as antibodies with which a sandwich EIA system can be prepared together with F1033-3-1 antibody were selected F1023-1-1 (rat IgG1), F1031-7-1 (mouse IgG1), and 3C10 antibodies. Similarly, as antibodies with which a sandwich EIA system can be prepared together with F1025-3-1 antibody were selected F1023-1-1 (rat IgG1) and 3C10 antibodies.

(2) Establishment of Sandwich ELISA System

Figure 3:
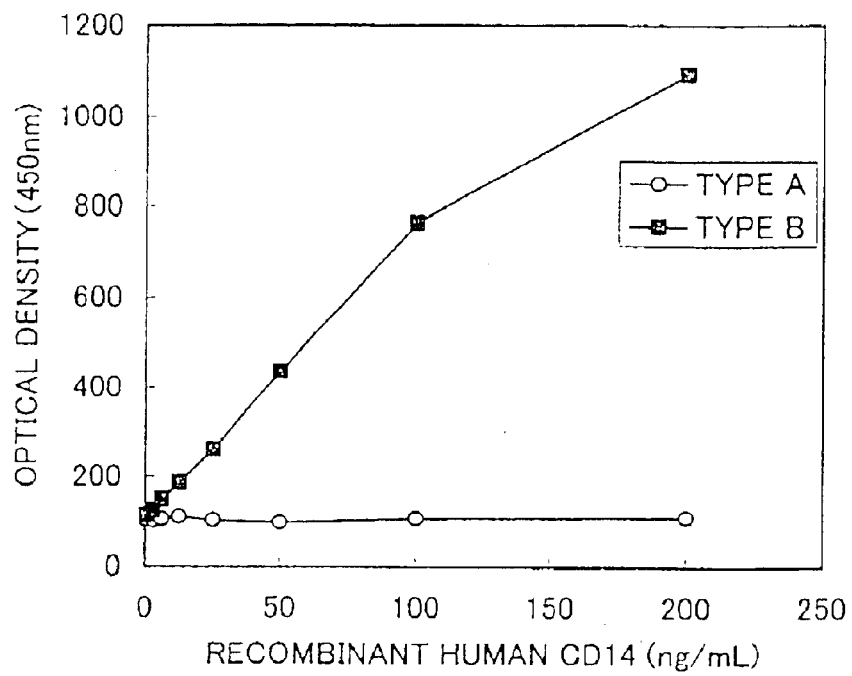
FIG. 3 is a diagram illustrating results of measurement of sandwich ELISA system using monoclonal antibody F1033-3-1 and F1023-1-1 antibody by an ELISA method based on the reactivity with recombinant human CD14 proteins. Type A and Type B indicate reactivities with high molecular weight soluble CD14 protein of the type that has a length of the full length minus 28 amino acids and high molecular full-length soluble CD14 protein, respectively.
Figure 4:
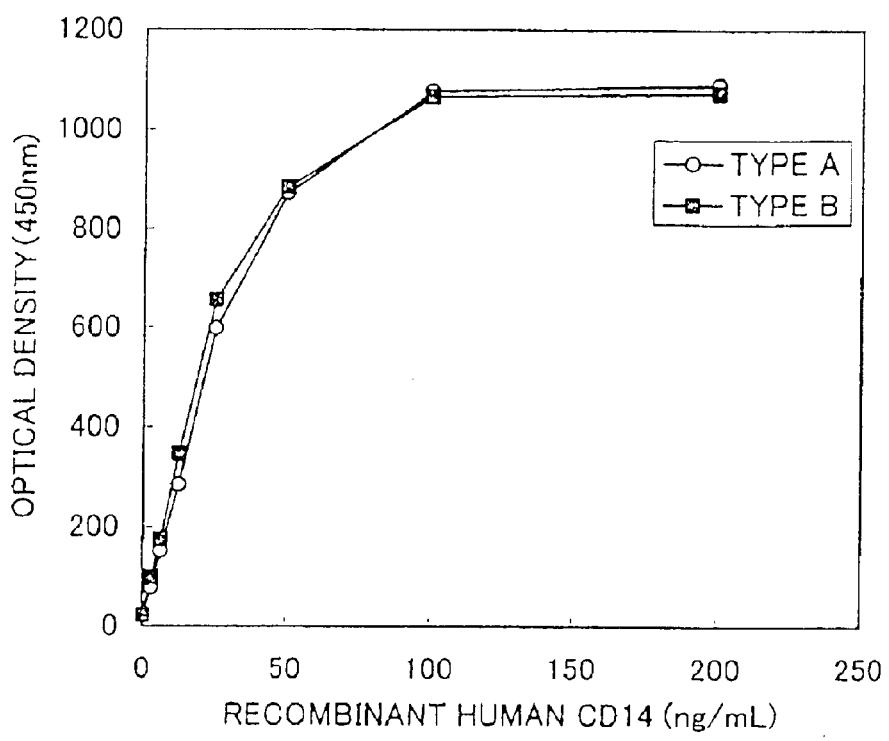
FIG. 4 is a diagram illustrating results of measurement of the specificity of monoclonal antibody F1025-3-1 and F1023-1-1 antibody by an ELISA method based on the reactivity with recombinant human CD14 proteins. Type A and Type B indicate reactivities with high molecular weight soluble CD14 protein of the type that has a length of the full length minus 28 amino acids and high molecular full length soluble CD14 protein, respectively.

Purified F1023-1-1 antibody was diluted with 0.01 M carbonate buffer (pH 9.0) to 10 μl/ml and 50 μl of the solution was added to each well of Immunoplate (Maxisorb, NUNC). After 1 hour's reaction at 25° C., the plate was washed 5 times with deionized water and 100 μl of 0.05 M phosphate buffer (pH 7.4) (hereinafter, described as PBS(-)) containing 0.5% BSA was added to each well to effect blocking. A standard preparation of high molecular weight soluble CD14 protein was diluted with PBS(-) containing 1% CD14 protein absorption serum 0.1% BSA to make a dilution series ranging from 0 to 100 ng/ml. The specimen were diluted 100-fold with PBS(-) containing 0.1% BSA. The dilution series of standard preparation or diluted specimen was added to the plate in an amount of 25 μl/well and further 25 μl/well of the diluent was added. Thereafter, reaction was allowed to proceed at 25° C. for 1 hour. Then, the plate was washed 3 times with physiological saline containing 0.05% Tween 20 and peroxidase labeled F1033-3-1 antibody or peroxidase labeled F1025-3-1 antibody, diluted with PBS(-) containing 10% rat serum and 0.1% Tween 20 to 0.5 to 2 μg/ml was added to each well in an amount of 50 al. After 1 hour's reaction at 25° C., the plate was washed 5 times in the same manner as above and a tetramethylbenzidine solution containing 0.01% hydrogen peroxide was added to each well, After 20 minutes' reaction at room temperature, the reaction was stopped with a 0.5 M sulfuric acid solution. The optical density at 450 nm was measured using a plate spectrophotometer (NJ-2100, Japan Intermed) and a standard curves were prepared. FIGS. 3 and 4 show the prepared standard curves. Each sensitivity of measurement was 0.5 ng/ml (blank+3SD), thus realizing a measurement system that is highly sensitive, simple and easy. To confirm the specificity of the prepared sandwich ELISA system, measurement was performed using the recombinant human CD14 proteins prepared in Example 4 in the above-described system. As a result, the measurement system using F1033-3-1 antibody enabled preparation of a standard curve only for type B high molecular weight soluble CD14 protein but did not react with type A high molecular weight soluble CD14 protein, so that the specificity of the present system was confirmed. With the measurement system using F1025-3-1 antibody, standard curves could be prepared for both type A and type B high molecular weight soluble CD14 proteins.

Example 9

Measurement of High Molecular Weight Soluble CD14 Proteins in Blood

Figure 5:
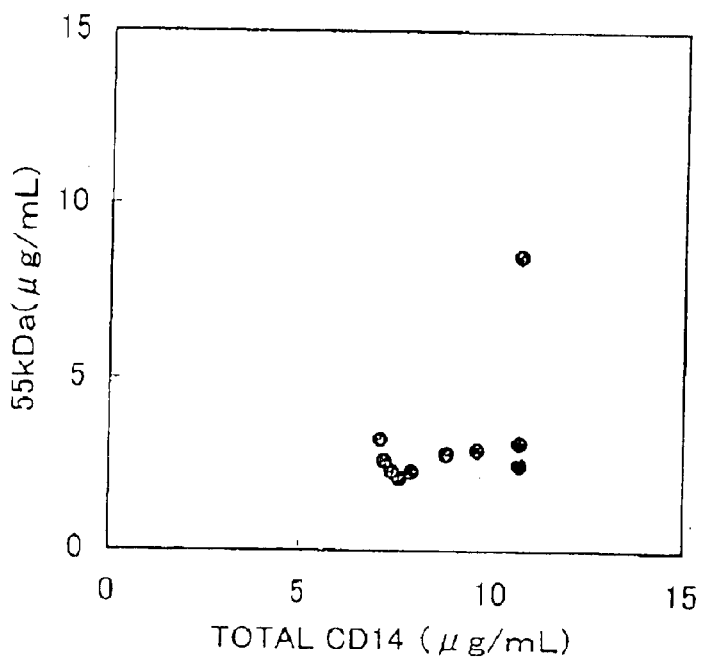
FIG. 5 is a diagram illustrating the relationship between all the soluble CD14 proteins obtained by measurement of soluble CD14 proteins from patients suffering from sepsis using a kit available from IBL Co. and CD14 55 kDa protein measured by sandwich ELISA using monoclonal antibody F1033-3-1 and F1023-1-1 antibody.

Measurement of serum was performed for 40 normal persons (20 males and 20 females) and 10 patients suffering from sepsis. Further, the total amount of soluble CD14 proteins was measured using sCD14 protein ELISA kit of IBL Co. (Hamburg). Comparing the measurement results obtained in the measurement system using F1023-1-1/F1033-3-1 antibody (amount of 55 kDa) with the total amount of soluble CD14 proteins, a high correlation with a correlation coefficient r=0.78 was observed between the total amount of soluble CD14 protein and the amount of 55 kDa type for normal persons. On the other hand, for patients suffering from sepsis, such correlation was not observed as shown in FIG. 5. The above results suggest that in the case of normal persons, major portion of soluble CD14 proteins in blood comprises a soluble CD14 55 KdA protein while in patients suffering from sepsis, although the 55 kDa type CD14 protein increases, low molecular weight soluble CD14 proteins that are not detected by the measurement system for measuring 55 kDa type CD14 protein varies.

Example 10

Analysis of Soluble CD14 Proteins in Blood (1) Quantitative Determination of Soluble CD14 Proteins in Blood of Normal Persons using Various CD14 Protein-ELISA Systems For the purpose of performing quantitative determination of respective subtypes of soluble CD14 proteins in blood sera of normal persons, the respective subtypes were isolated from sera and measured by an immunoassay system using the prepared antibodies.

First, about 20 ml of serum from a normal person was centrifuged and filtered through a 0.45 μm membrane, and subjected to column to which 3C10 antibody was bound that can bind with all the subtypes. Thereafter, the column was eluted with 0.1 M Glycine-HCl (pH 3.0). The eluted fractions were recovered and optical density at 280 nm were measured, from which concentrations of proteins were calculated.

Then, purified soluble CD14 protein (82 μl/ml) and three kinds of antibodies were mixed and subtypes of soluble CD14 proteins specific to the respective antibodies were absorbed. That is, 5 μg of purified soluble CD14 protein and 13.6 μg of 3C10, 1025-3-1 antibody or 1033-3-1 antibody were mixed and allowed to react at 4° C. for 18 hours. About 20 μl of resin to which protein G was bound (ProsepG, Millipore) was added to each solution and the resulting mixtures were shaken at room temperature for 1 hour to trap sCD14 protein/antibody complex. The supernatant of the reaction mixture was recovered and the amounts of high molecular weight soluble CDq4 proteins were measured. As a result, all the sCD14 proteins were absorbed with 3C10 antibody while 97% of sCD14 proteins was absorbed with 1025-3-1 antibody or 1033-3-1 antibody. From the above, it was elucidated that the content of low molecular weight soluble CD14 proteins in serum is about 3%.

(2) Isolation and Detection of Low Molecular Weight Soluble CD14 Proteins in Blood Human serum derived soluble CD14 protein was subjected to a column for affinity purification (HiTrap column (Amersham Pharmacia Biotech Co.)) to which was bound anti-human CD14 protein antibody (3C10) to effect selective absorption and eluted by pH gradient. The obtained eluted fractions were immediately neutralized with 1 M HEPES buffer of pH 8.0 to adjust pH to neutrality. Each fraction was detected by an EIA method using HRP-conjugated 3C10 and fractions that contain CD14 protein modified polypeptides were selected. Then, human serum derived low molecular weight soluble CD14 proteins were purified from human serum derived soluble CD14 proteins by the following method. That is, samples were stepwise purified by subjecting them to a column for affinity purification (HiTrap column (Amersham Pharmacia Biotech Co.)) to which was bound an antibody (F1033-3-1) that recognizes 55 kDa CD14 protein and then to a column for affinity purification to which was bound an antibody (F1025-3-1) that recognizes 49 kDa. The obtained eluted fractions and non-adsorbed fractions were concentrated by a freeze-drying method and the concentration of protein was measured by an EIA method using anti-CD14 protein antibody.

Figure 6:
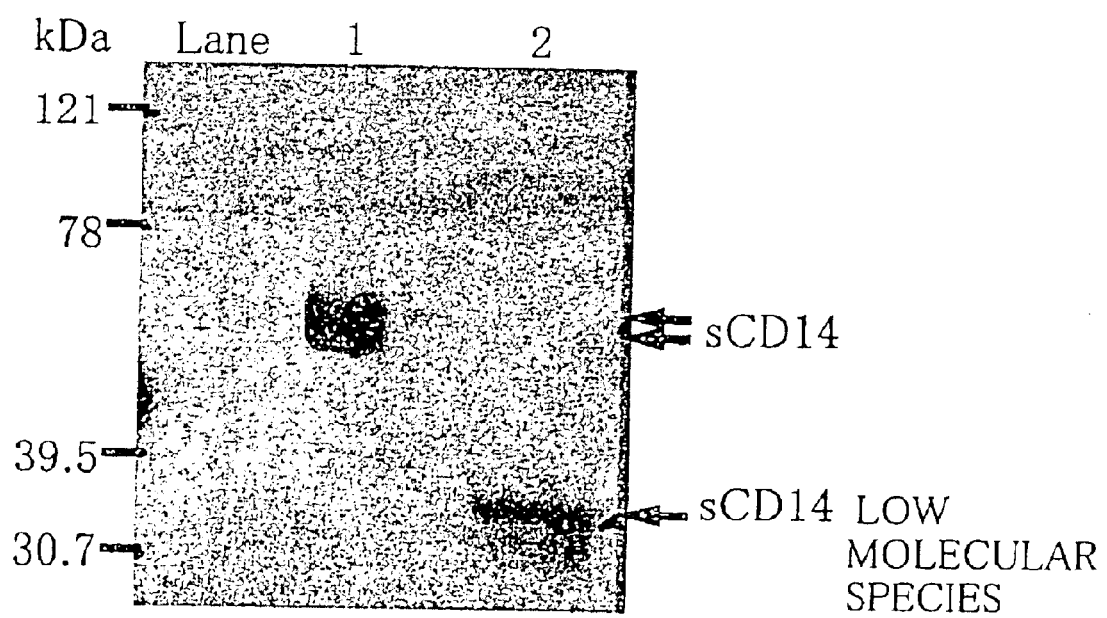
FIG. 6 is a diagram illustrating results of Western blotting obtained by detecting separated and purified human serum derived soluble CD14 protein with an anti-CD14 protein antibody.

The molecular weight of each fraction of the obtained human serum derived soluble CD14 protein was confirmed by Western blotting using anti-human CD14 protein antibodies (3C10 and MEM-18). That is, 30 ng/lane of each fraction of the obtained human serum derived soluble CD14 protein was electrophoresed on SDS-polyacrylamide gradient gel (5 to 20%, ATTO Co.), transferred onto PVDF membrane (Japan Millipore Co.), subjected to blocking reaction with 30 ml of PBS(−) containing 0.5% skim milk at room temperature for 1 hour, and allowed to react at room temperature for 1 hour after addition of 10 μg/ml of 3C10 and 100-fold diluted MEM-18. Further, the reaction product was allowed to react with HRP-conjugated anti-mouse IgG antibody at room temperature for 30 minutes and thereafter detected using ECL kit (Amersham Pharmacia Biotech Co.). FIG. 6 shows the results of analysis.

As a result, human serum derived high molecular weight soluble CD14 protein has bands detected at the positions of 49 kDa and 55 kDa (Lane 1) and human serum derived low molecular weight soluble CD14 protein has a band detected at the position of 36 kDa (Lane 2).

Furthermore, the reason why no 36 kDa molecule was detected in human serum derived soluble CD14 protein (Lane 1) is because 36 kDa molecule is contained in human serum derived soluble CD14 protein in minute amounts as compared with 49 kDa and 55 kDa molecules.

Example 11

Behavior of Low Molecular Weight Soluble CD14 Proteins in Normal Persons and Patients Suffering From Sepsis Using sera from normal persons and patients suffering from sepsis, the total amount of soluble CD14 proteins in blood was measured with a soluble CD14 protein ELISA kit of IBL Co. (Hamburg). Also, using the measurement system for measuring high molecular weight soluble CD14 proteins described in Example 8, only high molecular weight soluble CD14 protein were measured. To compare values measured by the both kits with each other, the standard used in the soluble CD14 protein ELISA kit of IBL Co. (Hamburg) were measured using the measurement system for measuring high molecular weight soluble CD14 proteins and the measured values of standard were compared. As a result, measured value of high molecular weight soluble CD14 protein×2.16 was calculated as a corrected value. Using this corrected value, the measured values measured by the measurement system for measuring high molecular weight soluble CD14 proteins were corrected, and the amount of high molecular weight soluble CD14 proteins was subtracted from the total amount measured by sCD14 protein ELISA kit of IBL Co. (Hamburg) to obtain the amount of low molecular weight soluble CD14 proteins. FIG. 7 shows the results, which demonstrated that almost no low molecular weight soluble CD14 protein was detected in normal persons whereas in patients suffering from sepsis, it tends to be at high levels and low molecular weight soluble CD14 proteins can be a new marker for patients suffering from sepsis.

Example 12

Isolation and Detection of Low Molecular Weight Soluble CD14 Proteins in Human Urine After removing insoluble matter in urine through a 0.22 μm PVDF membrane, the urine was subjected to a column for affinity purification (CNBR-activated Sepharose™ 4 FastFlow column (Amersham Pharmacia Biotech Co.)) to which was bound anti-human CD14 antibody (3C10) to effect selective absorption and the column was eluted by pH gradient. The obtained fractions were immediately neutralized with 7.5% sodium bicarbonate buffer to adjust pH to neutrality. Each fraction was detected by an EIA method using HRP-conjugated 3C10 and fractions that contain soluble CD14 proteins in human urine were selected. Then, purification of human urine low molecular weight soluble CD14 proteins in human urine from soluble CD14 proteins was stepwise performed by subjecting samples to a column for affinity purification to which was bound an antibody (F1025-3-1) that recognizes a sequence of from the 316th position to the 345th position of soluble CD14 protein. The obtained eluted fractions and non-adsorbed fractions were concentrated by a freeze-drying method and the concentration of protein was measured by an EIA method using anti-human CD14 antibody.

Analysis of low molecular weight soluble CD14 proteins in human urine was confirmed by Western blotting according to Example 10(2).

As a result, high molecular weight soluble CD14 proteins were detected between 49 kDa and 55 kDa and low molecular weight soluble CD14 proteins have a plurality of bands detected between 7.7 kDa and 42 kDa including a band at the position of 36 kDa. This suggests that in urine like in blood, high molecular weight soluble CD14 proteins and low molecular weight soluble CD14 proteins are present.

Industrail Applcability

According to the present invention the antibody to, high molecular weight soluble CD14 proteins are obtained. Use of the antibody makes it possible to simply and easily practice detection and quantitative determination of high molecular weight soluble CD14 proteins with high sensitivity, high precision and high specificity. Furthermore, use of the antibody enables and quantitative determination of low molecular weight soluble CD14 proteins. According to the present invention, it is possible to simply and easily diagnose diseases such as sepsis for which soluble CD14 proteins or low molecular weight soluble CD14 proteins serve as an index.

What is claimed is:

1. A method for diagnosing sepsis in a patient comprising the steps of:
   measuring an amount of low molecular weight soluble CD14 proteins in a body fluid sample from the patient, wherein said low molecular weight soluble CD14 proteins have an amino acid sequence wherein 42 or more amino acids from the C-terminus of the amino acid sequence of human full length soluble CD14 protein, SEQ ID NO: 1, are deleted, and
   comparing the measured amount to a standard amount measured in body fluid samples of normal persons or patients in order to diagnose sepsis in the patient.

2. The method according to claim 1, wherein the low molecular weight soluble CD14 proteins do not bind to F1025-3-1 antibody as produced by a hybridoma cell line deposited as FERM BP-7296.

3. The method according to claim 1, wherein the low molecular weight soluble CD14 proteins are primarily 36 kDa proteins.

4. A method for measuring low molecular weight soluble CD14 proteins in a body fluid, wherein said low molecular weight soluble CD14 proteins have an amino acid sequence wherein 42 or more amino acids from the C-terminus of the amino acid sequence of human full length soluble CD14 protein are deleted, comprising the steps of:

(A) measuring immunologically a total amount of soluble CD14 proteins in the body fluid;

(B) measuring immunologically an amount of high molecular weight soluble CD14 proteins in the body fluid, wherein said high molecular weight soluble CD14 proteins are human full length soluble CD14 protein or soluble CD14 proteins having an amino acid sequence wherein 41 or less amino acids from the C-terminus of the amino acid sequence of human full length soluble CD14 protein, SEQ ID NO: 1, are deleted; and (C) calculating an amount of low molecular weight soluble CD14 proteins in the body fluid by subtracting the amount of high molecular weight soluble CD14 proteins from the total amount of soluble CD14 proteins.

5. The method according to claim 4, wherein said step (A) comprises specifically reacting the body fluid to a first anti-CD14 antibody and measuring first antibody-bound amount of soluble CD14 proteins; and said step (B) comprises specifically reacting the body fluid to a second anti-CD14 antibody different from the first antibody which binds to an amino acid sequence of from positions 316 to 328 of SEQ ID NO: 1 and measuring second antibody-bound amount of soluble CD14 proteins as indicative of the amount of high molecular weight soluble CD14 proteins.

6. The method according to claim 5, wherein each of said step (A) and said step (B) are an immunological sandwich method, that comprises the reacting step and the measuring step.

7. The method according to claim 4, wherein the low molecular weight soluble CD14 proteins do not bind to F1025-3-1 antibody as produced by a hybridoma cell line deposited as FERM BP-7296, but the high molecular weight soluble CD14 proteins bind to the F1025-3-l antibody.

8. The method according to claim 4, wherein the low molecular weight soluble CD14 proteins are primarily 36 kDa protein and the high molecular weight soluble CD14 proteins are primarily 49 kDa and 55 kDa proteins.

9. A method for selectively measuring high molecular weight soluble CD14 proteins in a body fluid sample from a patient comprising both high and low molecular weight soluble CD14 proteins, wherein said high molecular weight soluble CD14 proteins are human full length soluble CD14 proteins or soluble CD14 proteins having an amino acid sequence wherein 41 or less amino acids from the C-terminus of the amino acid sequence of human full length soluble CD14 protein, SEQ ID NO: 1, are deleted, comprising the steps of:

specifically reacting the body fluid to an anti-CD14 antibody which selectively binds to an amino acid sequence of from positions 316 to 356 of SEQ ID NO: 1, and measuring the antibody-bound amount of CD14 proteins, the antibody-bound amount being indicative of the amount of high molecular weight soluble CD14 proteins in the body fluid sample.

10. The method according to claim 9, wherein the anti-CD14 antibody binds to an amino acid sequence of from positions 316 to 328 of SEQ ID NO: 1, or from positions 331 to 345 of SEQ ID NO: 1.

11. The method according to claim 10, wherein the anti-CD14 antibody binds to an amino acid sequence of from positions 316 to 328 of SEQ ID NO: 1, and the high molecular weight soluble CD14 proteins are primarily mainly 49 kDa and 55 kDa proteins.

12. The method according to claim 10, wherein the anti-CD14 antibody binds to an amino acid sequence of from positions 331 to 345 of SEQ ID NO: 1, and the high molecular weight soluble CD14 proteins are primarily 55 kDa proteins.

13. An isolated antibody prepared by immunizing a mammal with a peptide consisting of amino acids 316-328 or amino acids 331–345 of SEQ ID NO: 1.

14. An antibody produced by a hybridoma cell line deposited as Accession No. FERM BP-7295 or Accession No. FERM BP-7296.

15. A hybridoma cell line deposited as Accession No. FERM BP-7295 or Accession No. FERM BP-7296.

* * * * *